(12) United States Patent
Chen et al.

(10) Patent No.: US 6,787,351 B2
(45) Date of Patent: Sep. 7, 2004

(54) ADENOVIRUS CARRYING GAG GENE HIV VACCINE

(75) Inventors: Ling Chen, Blue Bell, PA (US); John W. Shiver, Doylestown, PA (US); Andrew J. Bett, Lansdale, PA (US); Danilo R. Casimiro, Harleysville, PA (US); Michael J. Caulfield, Fort Washington, PA (US); Michael A. Chastain, Glenside, PA (US); Emilio A. Emini, Strafford, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/818,443

(22) Filed: Mar. 27, 2001

(65) Prior Publication Data

US 2002/0061517 A1 May 23, 2002

Related U.S. Application Data

(63) Continuation-in-part of application No. PCT/US00/18332, filed on Jul. 3, 2000.
(60) Provisional application No. 60/148,981, filed on Aug. 13, 1999, and provisional application No. 60/142,631, filed on Jul. 6, 1999.

(51) Int. Cl.$^7$ .................. C12N 15/74; C12N 15/09; C12P 21/06; A61K 48/00
(52) U.S. Cl. .................. 435/320.1; 435/69.1; 435/69.2; 424/93.2
(58) Field of Search .................. 435/320.1, 69.1, 435/69.2; 424/93.2

(56) References Cited

U.S. PATENT DOCUMENTS

| | | | |
|---|---|---|---|
| 5,643,579 A | 7/1997 | Hung et al. | |
| 5,672,508 A | 9/1997 | Gyuris et al. | 435/320.1 |
| 5,716,613 A * | 2/1998 | Guber et al. | 424/93.2 |
| 5,859,193 A | 1/1999 | Devare et al. | 530/350 |
| 6,019,978 A | 2/2000 | Ertl et al. | |
| 6,033,908 A | 3/2000 | Bout et al. | |
| 6,287,571 B1 | 9/2001 | Ertl et al. | 424/199.1 |

FOREIGN PATENT DOCUMENTS

| | | |
|---|---|---|
| EP | 0 586 076 A2 | 7/1993 |
| EP | 0 638 316 A1 | 7/1994 |
| EP | 0 707 071 | 8/1995 |
| WO | WO96/21015 | 7/1996 |
| WO | WO96/39178 | 12/1996 |
| WO | WO97/00326 | 1/1997 |
| WO | WO97/31115 | 8/1997 |
| WO | WO97/39771 | 10/1997 |
| WO | WO97/48370 | 12/1997 |
| WO | WO98/34640 | 8/1998 |
| WO | WO98/56919 | 12/1998 |
| WO | WO01/21201 A2 | 9/2000 |
| WO | WO01/02067 | 1/2001 |
| WO | WO01/43693 | 6/2001 |
| WO | WO01/45748 | 6/2001 |

OTHER PUBLICATIONS

Chroboczek, J. et al. "The Sequence of the Genome of Adenovirus Type 5 and Its Comparison with the Genome of Adenovirus Type 2", 1992, Virology, vol. 186, pp. 280–285.
Hitt, M. et al. "Human Adenovirus Vectors for Gene Transfer into Mammalian Cells", 1997, Advances in Pharmacology, vol. 40, pp. 137–206.

(List continued on next page.)

Primary Examiner—Hankyel T. Park
(74) Attorney, Agent, or Firm—Anna L. Cocuzzo; Jack L. Tribble

(57) ABSTRACT

An adenoviral vector is described which carries a codon-optimized gag gene, along with a heterologous promoter and transcription terminator. This viral vaccine can effectively prevent HIV infection when administered to humans either alone or as part of a prime and boost regime also with a vaccine plasmid.

20 Claims, 26 Drawing Sheets

OTHER PUBLICATIONS

Graham, F. et al. "Characteristics of a Human Cell Line Transformed by DNA from Human Adenovirus Type 5", 1977, J. Gen. Virol., vol. 36, pp. 59–74.

Myers, G. et al. "Human Retroviruses and AIDS 1995 : A compilation and Analysis of Nucleic Acid and Amino Acid Sequences", 1995, Part II, A3–A19.

Chapman, B. et al. "Effect of intron A from human cytomegalovirus (Towne) immediate–early gene on heterologous expression in mammalian cells", 1991, Nucleic Acids Resarch, vol. 19, pp. 3979–3986.

Montgomery, D. et al. "Heterologous and Homologous Protection Against Influenza A by DNA Vaccination: Optimization of DNA Vectors", 1993, DNA and Cell Biology, vol. 12, pp. 777–783.

Grable, M. et al. "Adenovirus Type 5 Packaging Domain Is Composed of a Repeated Element That is Functionally Redundant", Journal of Virology, 1990, vol. 64, pp. 2047–2056.

Grable, M. et al. "cis and trans Requirements for the Selective Packaging of Adenovirus Type 5 DNA", Journal of Virology, 1992, vol. 66, pp. 723–731.

Wang, Y. et al. "The Use of an E1–Deleted, Replication–Defective Adenovirus Recombinant Expressing the Rabies Virus Glycoprotein for Early Vaccination of Mice against Rabies Virus", Journal of Virology, 1997, vol. 71, pp. 3677–3583.

Natuk, R. et al. "Immunogenicity of Recombinant Human Adenovirus–Human Immunodeficiency Virus Vaccines in Chimpanzees", AIDS Research and Human Retroviruses, 1993, vol. 9, pp. 395–404.

Prevec, L. et al. "Immune Response to HIV–1 gag Antigens Induced by Recombinant Adenovirus Vectors in Mice and Rhesus Macaque Monkeys", Journal of Acquired Immune Deficiency Syndrome, 1991, vol. 4, pp. 568–576.

Lori, F. et al. "Rapid protection against human immunodeficiency virus type 1 (HIV–1) replication mediated by high efficiency non–retroviral delivery of genes interfering with HIV–1 tat and gag", Gene Therapy, 1994, vol. 1, pp. 27–31.

Pfarr, D. et al. "Differential Effects of Polyadenylation Regions on Gene Expression in Mammalian Cells", DNA, 1986, vol. 5, pp. 115–122.

Natuk, R. et al. "Adenovirus Vectored Vaccines", Developments in Biological Standardization, 1994, vol. 82, pp. 71–77.

Aiken, C. et al. "Nef Induces CD4 Endocytosis: Requirement for a Critical Dileucine Motif in the Membrane–Proximal CD4 Cytoplasmic Domain", Cell, 1994, vol. 76, pp. 853–864.

Davies, J. et al. "Crystal Structure of the Ribonuclease H Domain of HIV–1 Reverse Transcriptase", Science, 1991, vol. 252, pp. 88–95.

Franchini, G. et al. "Cytoplasmic Localization of the HTLV–III 3'orf Protein in Cultured T Cells", Virology, 1986, vol. 155, pp. 593–599.

Larder, B. et al. "Infectious potential of human immunodeficiency virus type 1 reverse transcriptase mutants with altered inhibitor sensitivity", Proc. Natl. Acad. Sci. USA, 1989, vol. 86, pp. 4803–4807.

Larder, B. et al. "Site–specific mutagenesis of AIDS virus reverse transcriptase", Nature, 1987, vol. 327, pp. 716–717.

Lathe, R. "Synthetic Oligonucleotide Probes Deduced from Amino Acid Sequence Data Theoretical and Practical Considerations", Journal Molecular Biology, 1985, vol. 183, pp. 1–12.

Leavitt, A. et al. "Site–directed Mutagenesis of HIV–1 Integrase Demonstrates Differential Effects on Integrase Functions in Vitro", The Journal of Biological Chemistry, 1993, vol. 268, pp. 2113–2119.

Miyahira, Y. et al. "Quantification of antigen specific CD8+ T cells using an ELISPOT assay", Journal of Immunological Methods, 1995, vol. 181, pp. 45–54.

Mizrahi, V. et al. "Site–directed mutagenesis of the conserved Asp–443 and Asp–498 carboxy–terminal residues of HIV–1 reverse Transcriptase", Nucleic Acids Research, 1990, vol. 18, pp. 5359–5363.

Ondoa, P. et al. "Evaluation of Different V3 Peptides in an Enzyme Immunoassay for Specific HIV Type 1 Group O Antibody Detection", Aids Research and Human Retroviruses, 1998, vol. 14, pp. 963–972.

Schatz, O. et al. "Point mutations in conserved amino acid residues within the C–terminal domain of HIV–1 reverse transcriptase specifically repress RNase H function, " FEBS Letters, 1989, vol. 257, pp. 311–314.

Schwartz, O. et al. "Endocytosis of major histocompatibility complex I molecules is induced by the HIV–1 Nef protein", Nature Medicine, 1996, vol. 2, pp. 338–342.

Wiskerchen, M. et al. "Human Immunodeficiency Virus Type 1 Integrase: Effects of Mutations on Viral Ability To Integrate, Direct Viral Gene Expression from Unintegrated Viral DNA Templates, and Sustain Viral Propagation in Primary Cells", Journal of Virology, 1995, vol. 69, pp. 376–386.

Fallaux, F. et al. "New Helper Cells and Matched Early Region 1–Deleted Adenovirus Vectors Prevent Generation of Replication–Competent Adenoviruses", Human Gene Therapy, 1998, vol. 9, pp. 1909–1917.

Flanagan, B. et al., "A recombinant human adenovirus expressing the simian immunodeficiency virus Gag antigen can induce long–lived immune responses in mice", Journal of General Virology, 1997, vol. 78, pp. 991–997.

Lubeck, M. et al. "Immunogenicity of Recombinant Adenovirus–Human Immunodeficiency Virus Vaccines in Chimpanzees Following Intranasal Administration", AIDS Research and Human Retroviruses, 1994, vol. 10, pp. 1443–1449.

Vernon, S. et al. "Ultrastructural characterization of human immunodeficiency virus type 1 Gag–containing particles assembled in a recombinant adenovirus vector system", Journal of General Virology, 1991, vol. 72, pp. 1243–1251.

* cited by examiner

Optimized HIV-1 (CAM1) *gag* orf

```
   1 AGATCTACCA TGGGTGCTAG GGCTTCTGTG CTGTCTGGTG GTGAGCTGGA
  51 CAAGTGGGAG AAGATCAGGC TGAGGCCTGG TGGCAAGAAG AAGTACAAGC
 101 TAAAGCACAT TGTGTGGGCC TCCAGGGAGC TGGAGAGGTT TGCTGTGAAC
 151 CCTGGCCTGC TGGAGACCTC TGAGGGGTGC AGGCAGATCC TGGGCCAGCT
 201 CCAGCCCTCC CTGCAAACAG GCTCTGAGGA GCTGAGGTCC CTGTACAACA
 251 CAGTGGCTAC CCTGTACTGT GTGCACCAGA AGATTGATGT GAAGGACACC
 301 AAGGAGGCCC TGGAGAAGAT TGAGGAGGAG CAGAACAAGT CCAAGAAGAA
 351 GGCCCAGCAG GCTGCTGCTG GCACAGGCAA CTCCAGCCAG GTGTCCCAGA
 401 ACTACCCCAT TGTGCAGAAC CTCCAGGGCC AGATGGTGCA CCAGGCCATC
 451 TCCCCCCGGA CCCTGAATGC CTGGGTGAAG GTGGTGGAGG AGAAGGCCTT
 501 CTCCCCTGAG GTGATCCCCA TGTTCTCTGC CCTGTCTGAG GGTGCCACCC
 551 CCCAGGACCT GAACACCATG CTGAACACAG TGGGGGGCCA TCAGGCTGCC
 601 ATGCAGATGC TGAAGGAGAC CATCAATGAG GAGGCTGCTG AGTGGGACAG
 651 GCTGCATCCT GTGCACGCTG GCCCCATTGC CCCCGGCCAG ATGAGGGAGC
 701 CCAGGGGCTC TGACATTGCT GGCACCACCT CCACCCTCCA GGAGCAGATT
 751 GGCTGGATGA CCAACAACCC CCCCATCCCT GTGGGGGAAA TCTACAAGAG
 801 GTGGATCATC CTGGGCCTGA ACAAGATTGT GAGGATGTAC TCCCCCACCT
 851 CCATCCTGGA CATCAGGCAG GGCCCCAAGG AGCCCTTCAG GGACTATGTG
 901 GACAGGTTCT ACAAGACCCT GAGGGCTGAG CAGGCCTCCC AGGAGGTGAA
 951 GAACTGGATG ACAGAGACCC TGCTGGTGCA GAATGCCAAC CCTGACTGCA
1001 AGACCATCCT GAAGGCCCTG GGCCCTGCTG CCACCCTGGA GGAGATGATG
1051 ACAGCCTGCC AGGGGGTGGG GGGCCCTGGT CACAAGGCCA GGGTGCTGGC
1101 TGAGGCCATG TCCCAGGTGA CCAACTCCGC CACCATCATG ATGCAGAGGG
1151 GCAACTTCAG GAACCAGAGG AAGACAGTGA AGTGCTTCAA CTGTGGCAAG
1201 GTGGGCCACA TTGCCAAGAA CTGTAGGGCC CCCAGGAAGA AGGGCTGCTG
1251 GAAGTGTGGC AAGGAGGGCC ACCAGATGAA GGACTGCAAT GAGAGGCAGG
1301 CCAACTTCCT GGGCAAAATC TGGCCCTCCC ACAAGGGCAG GCCTGGCAAC
1351 TTCCTCCAGT CCAGGCCTGA GCCCACAGCC CCTCCCGAGG AGTCCTTCAG
1401 GTTTGGGGAG GAGAAGACCA CCCCCAGCCA GAAGCAGGAG CCCATTGACA
1451 AGGAGCTGTA CCCCCTGGCC TCCCTGAGGT CCCTGTTTGG CAACGACCCC
1501 TCCTCCCAGT AAAATAAAGC CCGGGCAGAT CT
```

(SEQ ID NO:1)

FIG.6

TPA-GAG open reading frame

```
ATGGATGCAATGAAGAGAGGGCTCTGCTGTGTGCTGCTGCTGTGTGGAGCAGTCTTCG
TTTCGCCCAGCGAGATCTCCATTGTGTGGGCCTCCAGGGAGCTGGAGAGGTTTGCTGT
GAACCCTGGCCTGCTGGAGACCTCTGAGGGGTGCAGGCAGATCCTGGGCCAGCTCCAG
CCCTCCCTGCAAACAGGCTCTGAGGAGCTGAGGTCCCTGTACAACACAGTGGCTACCC
TGTACTGTGTGCACCAGAAGATTGATGTGAAGGACACCAAGGAGGCCCTGGAGAAGA
TTGAGGAGGAGCAGAACAAGTCCAAGAAGAAGGCCCAGCAGGCTGCTGCTGGCACAG
GCAACTCCAGCCAGGTGTCCCAGAACTACCCCATTGTGCAGAACCTCCAGGGCCAGAT
GGTGCACCAGGCCATCTCCCCCCGGACCCTGAATGCCTGGGTGAAGGTGGTGGAGGAG
AAGGCCTTCTCCCCTGAGGTGATCCCCATGTTCTCTGCCCTGTCTGAGGGTGCCACCCC
CCAGGACCTGAACACCATGCTGAACACAGTGGGGGGCCATCAGGCTGCCATGCAGAT
GCTGAAGGAGACCATCAATGAGGAGGCTGCTGAGTGGGACAGGCTGCATCCTGTGCA
CGCTGGCCCCATTGCCCCCGGCCAGATGAGGGAGCCCAGGGGCTCTGACATTGCTGGC
ACCACCTCCACCCTCCAGGAGCAGATTGGCTGGATGACCAACAACCCCCCCATCCCTG
TGGGGGAAATCTACAAGAGGTGGATCATCCTGGGCCTGAACAAGATTGTGAGGATGTA
CTCCCCCACCTCCATCCTGGACATCAGGCAGGGCCCCAAGGAGCCCTTCAGGGACTAT
GTGGACAGGTTCTACAAGACCCTGAGGGCTGAGCAGGCCTCCCAGGAGGTGAAGAAC
TGGATGACAGAGACCCTGCTGGTGCAGAATGCCAACCCTGACTGCAAGACCATCCTGA
AGGCCCTGGGCCCTGCTGCCACCCTGGAGGAGATGATGACAGCCTGCCAGGGGGTGG
GGGGCCCTGGTCACAAGGCCAGGGTGCTGGCTGAGGCCATGTCCCAGGTGACCAACTC
CGCCACCATCATGATGCAGAGGGGCAACTTCAGGAACCAGAGGAAGACAGTGAAGTG
CTTCAACTGTGGCAAGGTGGGCCACATTGCCAAGAACTGTAGGGCCCCCAGGAAGAA
GGGCTGCTGGAAGTGTGGCAAGGAGGGCCACCAGATGAAGGACTGCAATGAGAGGCA
GGCCAACTTCCTGGGCAAAATCTGGCCCTCCCACAAGGGCAGGCCTGGCAACTTCCTC
CAGTCCAGGCCTGAGCCCACAGCCCCTCCCGAGGAGTCCTTCAGGTTTGGGGAGGAGA
AGACCACCCCCAGCCAGAAGCAGGAGCCCATTGACAAGGAGCTGTACCCCCTGGCCTC
CCTGAGGTCCCTGTTTGGCAACGACCCCTCCTCCCAGTAA
```
SEQ ID NO:4

FIG.8

Longevity of Cellular Immune Responses in Rhesus Monkeys Immunized with FG Adenovirus HIV-1 gag (69 weeks after final boost)

| Grp # | vaccine (particles) T=0, 24 Wk | Monk # | T=32 Wk Unfractionated Medium | T=32 Wk Unfractionated Gag H | T=32 Wk CD4- Gag H | T=93 Wk Unfractionated Medium | T=93 Wk Unfractionated Gag H | T=93 Wk CD4- Gag H |
|---|---|---|---|---|---|---|---|---|
| 1 | FG FL-gag/ 10^11 | 96R044 | 0 | 950 | 768 | 4 | 584 | 521 |
|   |   | 96R045 | 1 | 239 | 841 | 5 | 800 | 1026 |
|   |   | 96R046 | 1 | 1566 | 2039 | 10 | 983 | 1162 |
|   |   | 96R053 | 1 | 570 | 559 | 4 | 656 | 640 |
|   |   | 96R054 | 1 | 510 | 164 | 6 | 455 | 295 |
|   |   | 96R057 | 3 | 1230 | 1538 | 14 | 723 | 805 |
| 2 | FG FL-gag/ 10^9 | 96R047 | 1 | 13 | 35 | 3 | 131 | 130 |
|   |   | 96R048 | 0 | 138 | 101 | 5 | 179 | 210 |
|   |   | 96R049 | 0 | 190 | 266 | 8 | 269 | 189 |
|   |   | 96R058 | 4 | 219 | 269 | 11 | 116 | 121 |
|   |   | 96R060 | 6 | 183 | 133 | 3 | 90 | 89 |
|   |   | 96R062 | 3 | 3 | 29 | 4 | 28 | 36 |
| 5 | FG FL-gag/ 10^7 | 96R050 | 9 | 94 | 86 | 13 | 35 | 56 |
|   |   | 96R051 | 6 | 118 | 41 | 13 | 70 | 46 |
|   |   | 96R052 | 1 | 54 | 74 | 6 | 38 | 53 |
| 6 | FG FL-gag/10^11 (adeno pre-exposed 1X) | 940125 | 5 | 89 | 528 | 8 | 195 | 119 |
|   |   | 940132 | 1 | 136 | 90 | 10 | 79 | 16 |
|   |   | 940149 | 31 | 348 | 296 | 14 | 75 | 158 |
| 7 | FG FL-gag/10^11 (adeno pre-exposed 3X) | 920145 | 1 | 421 | 336 | 5 | 189 | 154 |
|   |   | 920147 | 15 | 1074 | 1003 | 1 | 226 | 538 |
|   |   | 940217 | 4 | 65 | 8 | 4 | 16 | 10 |
| 8 | none | 96R063 | 0 | 1 | 0 | 5 | 1 | ND |
|   |   | 94R004 | 1 | 3 | 8 | 0 | 4 | ND |

FIG. 9

Prime/Boost Immunizations of Rhesus Monkeys Using DNA+ adjuvants Followed By Adenovirus

| Grp # | Priming Vaccine | Adjuvant | ID | Prebleed Medium | Prebleed gag H | T=22 wks 2 Wk Pre Boost Medium | T=22 wks 2 Wk Pre Boost gag H | T=26 wks 2 Wk Post ad5-gag Boost Medium | T=26 wks 2 Wk Post ad5-gag Boost gag H |
|---|---|---|---|---|---|---|---|---|---|
| 1 | V1Jns-FL-gag 5 mgs | none | 26 | 5 | 4 | 11 | 313 | 6 | 318 |
|   |   |   | 9G | 6 | 6 | 18 | 48 | 1 | 314 |
|   |   |   | 0G | 9 | 4 | 10 | 171 | 3 | 368 |
| 2 | V1Jns-FL-gag 5 mgs | AlPO4 700 mcg | 46 | 5 | 8 | 1 | 318 | 0 | 1400 |
|   |   |   | 6F | 4 | 15 | 9 | 384 | 3 | 976 |
|   |   |   | 3G | 11 | 6 | 4 | 99 | 1 | 753 |
| 3 | V1Jns-FL-gag 5 mgs | CRL1005 | 5G | 3 | 1 | 3 | 881 | 18 | 1418 |
|   |   |   | 6Q | 8 | 6 | 18 | 450 | 13 | 4410 |
|   |   |   | 79 | 3 | 8 | 6 | 234 | 20 | 3223 |
| 4 | Naïve |   | 1E | 6 | 6 | 20 | 15 | 30 | 23 |
|   |   |   | 20 | 6 | 4 | 1 | 1 | 3 | 3 |

FIG. 10

Longevity of T Cell Responses in Monkeys Following Immunization: ELIspot Responses at Week 70 (46 weeks post final boost)

| Group | Rhesus# | Vaccine (T= 0 wk) | Vaccine (T= 4 wk) | Vaccine (T= 8 wk) | Vaccine (T= 24 wk) | Week 28 SFC/10$^6$ cells | | | Week 70 SFC/10$^6$ cells | | |
|---|---|---|---|---|---|---|---|---|---|---|---|
| | | | | | | medium | gag pool H | CD4- gag pool H | medium | gag pool H | CD4- gag pool H |
| 1 | 087F | gag/DNA | gag/DNA | gag/DNA | Ad5/gag | 58 | 1416 | 1070 | 8 | 721 | 753 |
| | 111Q | | | | | 10 | 1191 | 1248 | 5 | 2710 | 1818 |
| | 029F | | | | | 20 | 879 | 820 | 11 | 1114 | 908 |
| | 96007 | | | | | 20 | 840 | 590 | 1 | 841 | 719 |
| | T283 | | | | | | | | | | |
| 2 | 96R003 | ad5/gag | none | none | Ad5/gag | 8 | 1261 | 1175 | 10 | 1210 | 1270 |
| | 96039 | | | | | 83 | 1439 | 584 | 3 | 441 | 249 |
| | T286 | | | | | 35 | 1209 | 588 | 3 | 636 | 264 |
| | S203 | | | | | 6 | 481 | 204 | 1 | 398 | 183 |

FIG. 11

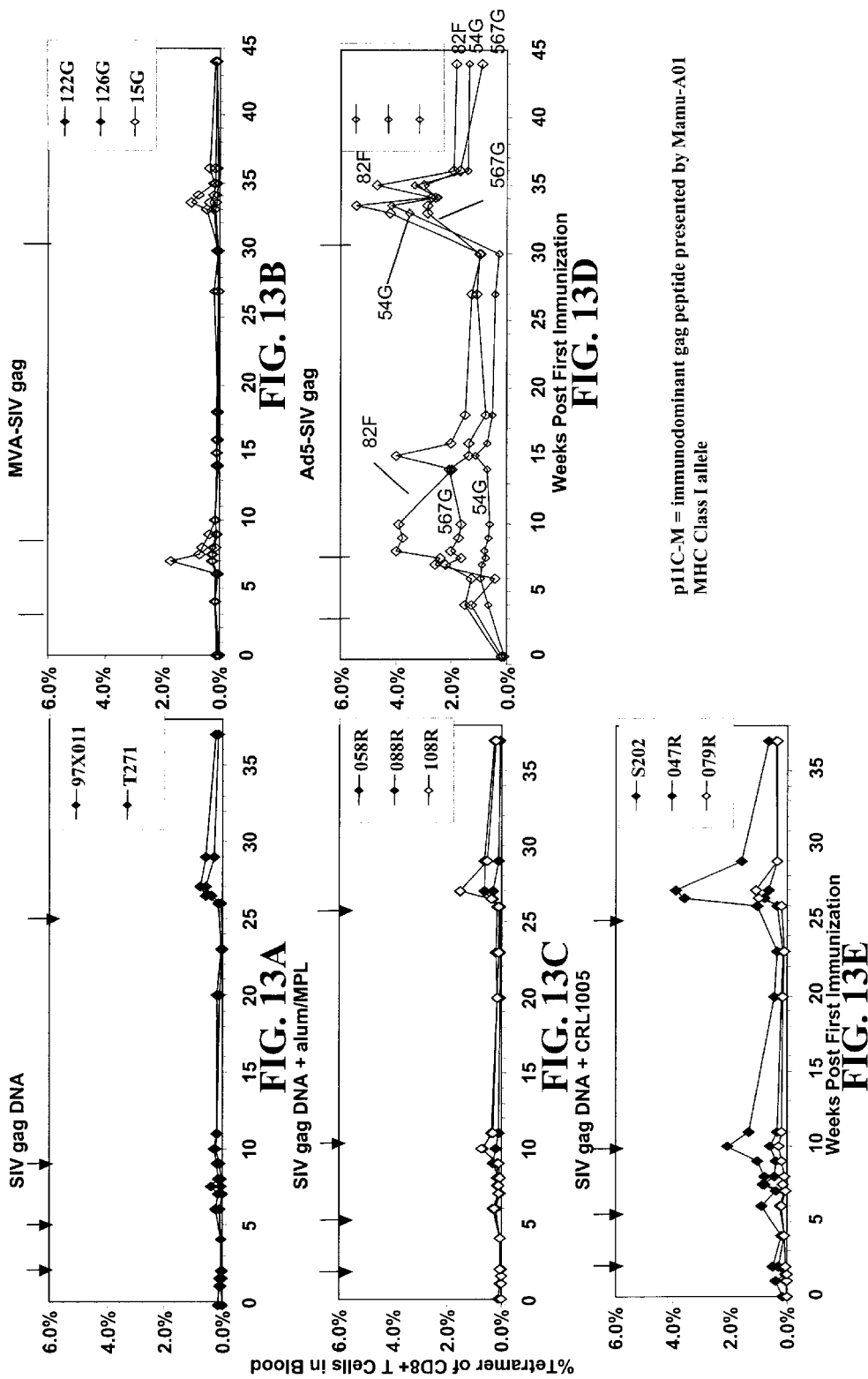

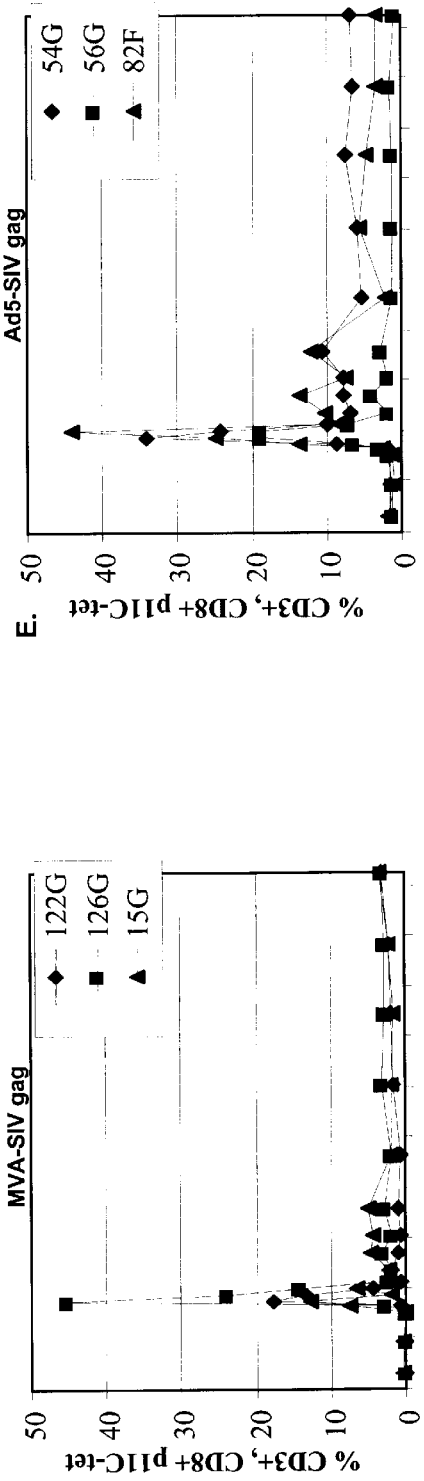
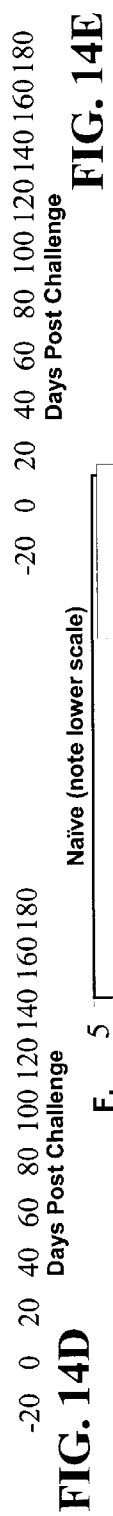
FIG. 14D
FIG. 14E
FIG. 14F

Pathogenic SHIV Challenge of Rhesus Monkeys Following gag Vaccinations
gag DNA Vaccinees ----- Assay Detection Limit > 500 vRNA copies/mL d185 Statistical Analysis F test ANOVA gives p<0.02

Monkey #
- ◆ 97X011
- ■ T271
- ▲ T282

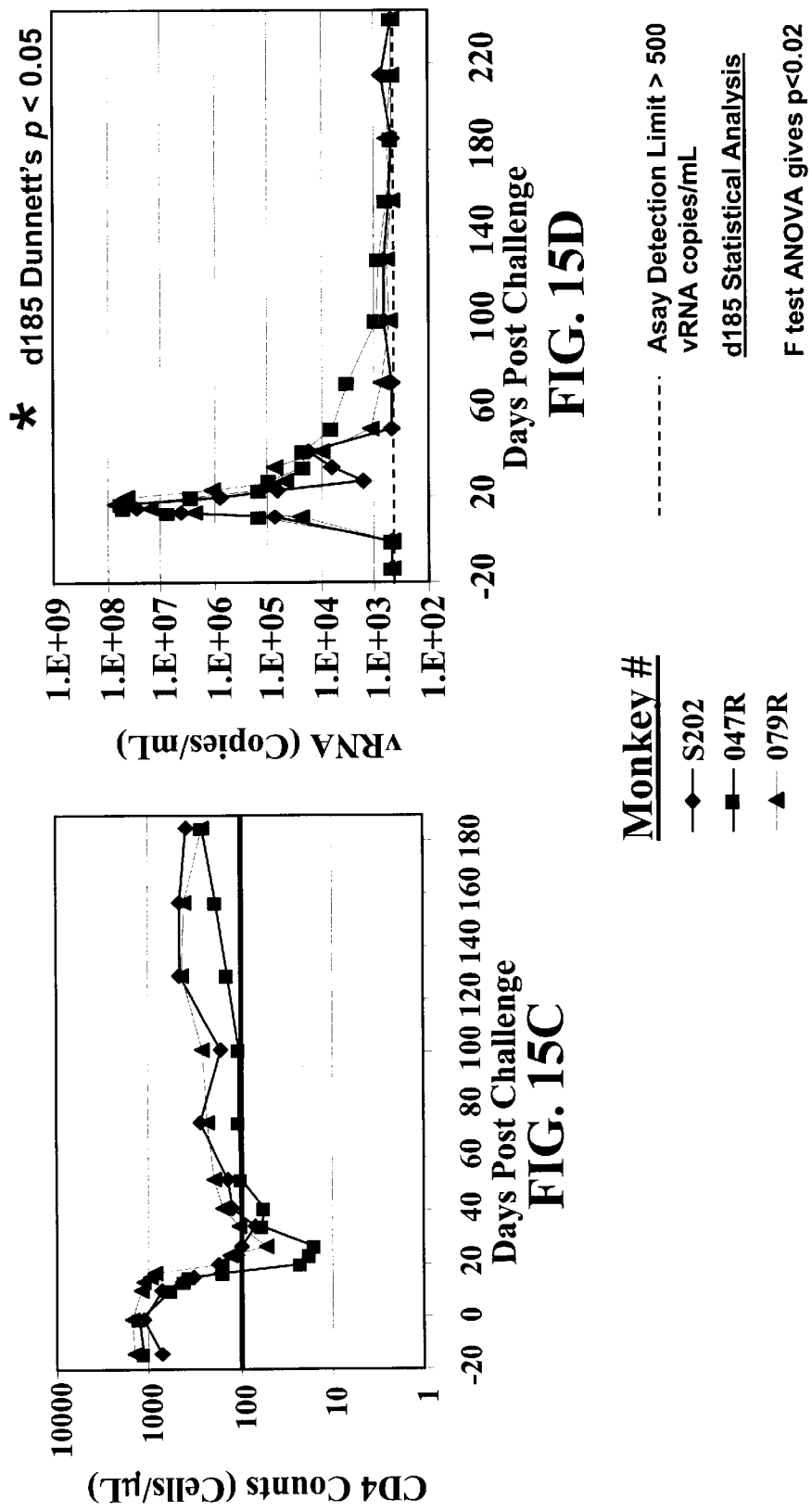

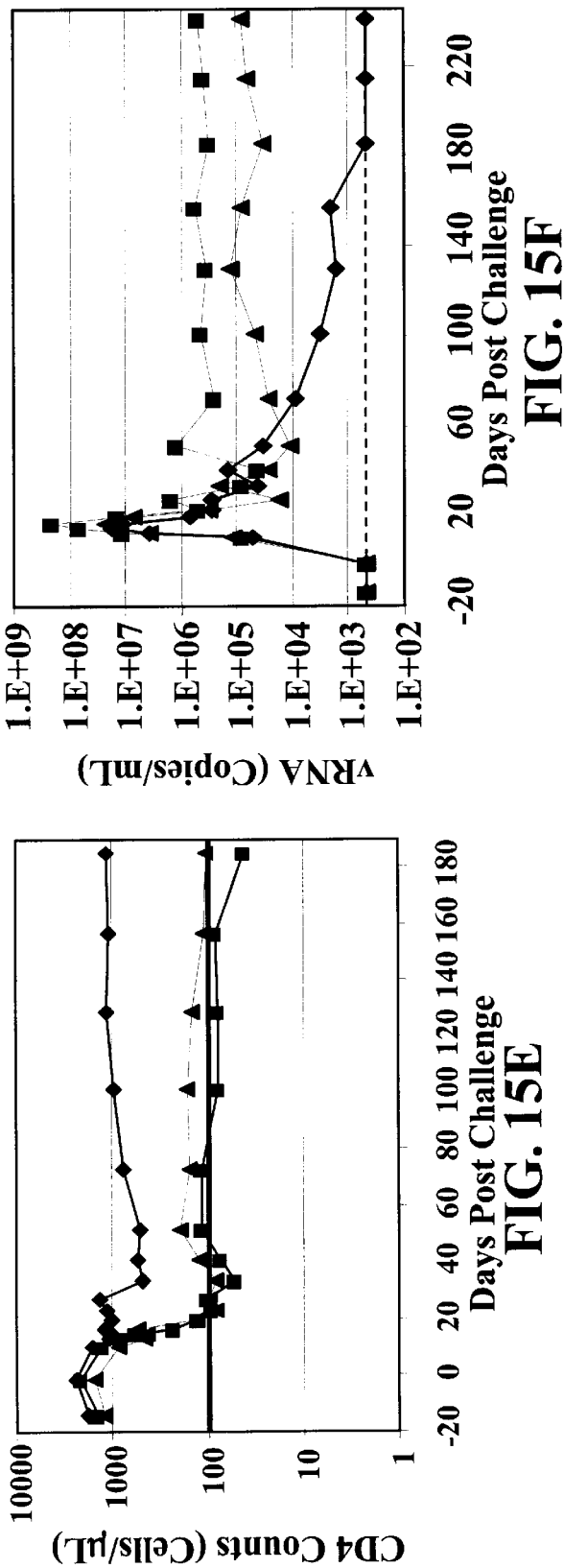

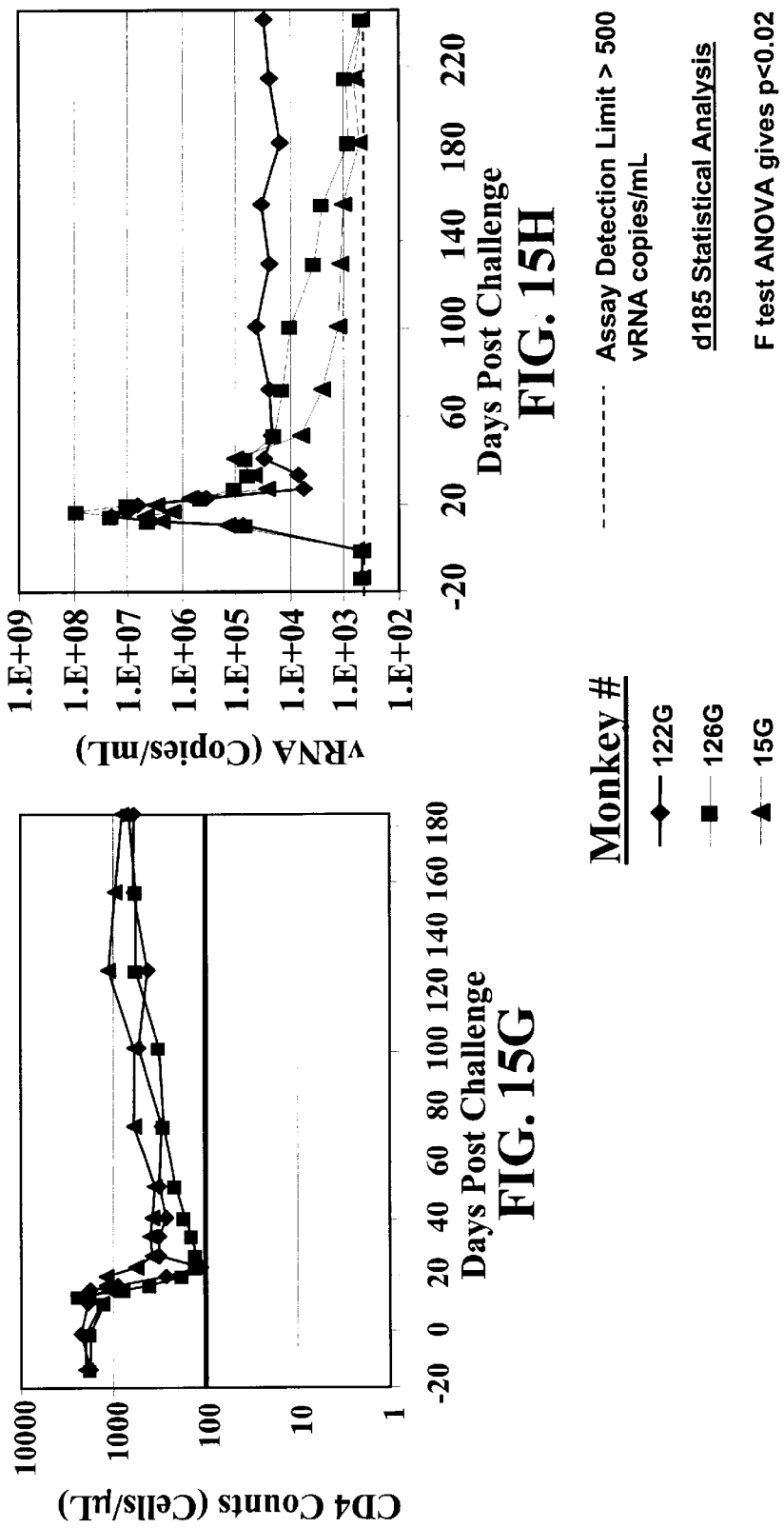

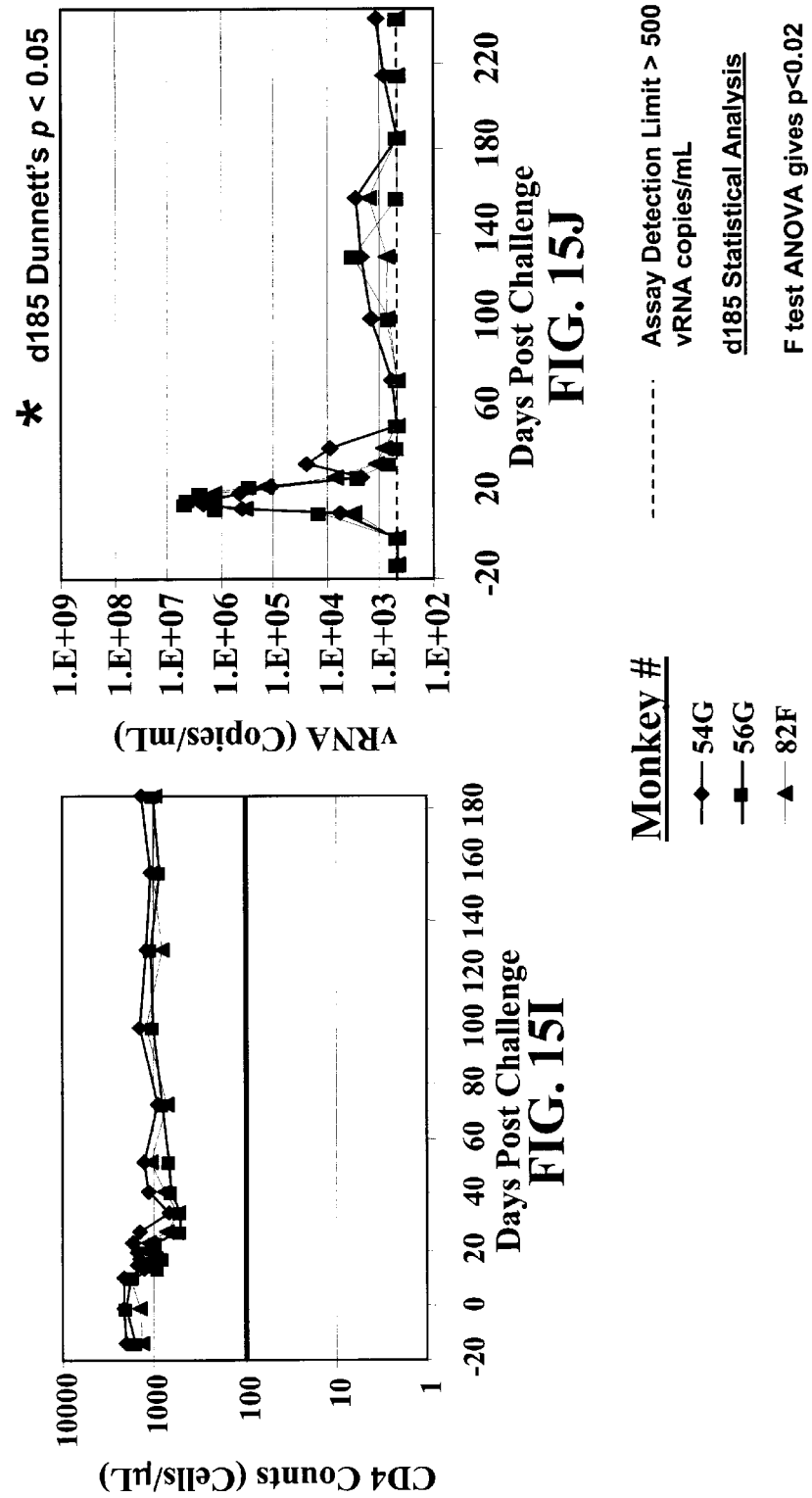

ADENOVIRUS CARRYING GAG GENE HIV VACCINE

CROSS REFERENCE TO RELATED APPLICATIONS

This application is a continuation-in-part of PCT International Application No. PCT/US00/18332, filed Jul. 3, 2000, which designates the U.S., which claims the benefit, under 35 U.S.C. §119(e), of U.S. Provisional Application Ser. No. 60/148,981, filed Aug. 13, 1999 and U.S. Provisional Application Ser. No. 60/142,631, filed Jul. 6, 1999.

FIELD OF THE INVENTION

This invention relates to replication deficient adenovirus vectors comprising an optimized human immunodeficiency virus (HIV) gag gene under the control of a strong promoter, which are suitable for vaccines against HIV.

BACKGROUND OF THE INVENTION

Human Immunodeficiency Virus-1 (HIV-1) is the etiological agent of acquired human immune deficiency syndrome (AIDS) and related disorders.

Vaccination is an effective form of disease prevention and has proven successful against several types of viral infection. However, determining ways to present HIV-1 antigens to the human immune system in order to evoke protective humoral and cellular immunity is a difficult task. In AIDS patients, free virus is present in low levels only. Transmission of HIV-1 is enhanced by cell-to-cell interaction via fusion and syncytia formation. Hence, antibodies generated against free virus or viral subunits are generally ineffective in eliminating virus-infected cells.

European Patent Applications 0 638 316 (Published Feb. 15, 1995) and 0 586 076 (Published Mar. 9, 1994), (both assigned to American Home Products Corporation) describe replicating adenovirus vectors carrying an HIV gene, including env or gag. Various treatment regimens were used with chimpanzees and dogs, some of which included booster adenovirus or protein plus alum treatments.

Infection with HIV-1 is almost always fatal, and at present there are no cures for HIV-1 infection. Effective vaccines for prevention of HIV-1 infection are not yet available. Because of the danger of reversion or infection, live attenuated virus probably cannot be used as a vaccine, and. subunit vaccine approaches have not been successful at preventing HIV infection. Treatments for HIV-1 infection, while prolonging the lives of some infected persons, have serious side effects. There is thus a great need for effective treatments and vaccines to combat this lethal infection.

SUMMARY OF THE INVENTION

This invention relates to a vaccine composition comprising a replication-defective adenoviral vector comprising at least one gene encoding an HIV gag protein, wherein the gene comprises codons optimized for expression in a human, and the gene is operably linked to a heterologous promoter.

Another aspect of this invention relates to an adenoviral vaccine vector comprising: a replication defective adenoviral genome, wherein the adenoviral genome does not have a functional E1 gene, and the adenoviral genome further comprises a gene expression cassette comprising:

i) a nucleic acid encoding a HIV gag protein, wherein the nucleic acid is codon optimized for expression in a human host;

ii) a heterologous promoter is operatively linked to the nucleic acid encoding the gag protein; and iii) a transcription terminator.

In preferred embodiments, the E1 gene has been deleted from the adenoviral vector, and the HIV expression cassette has replaced the deleted E1 gene. In other preferred embodiments, the replication defective adenovirus genome does not have a functional E3 gene, and preferably the E3 gene has been deleted.

This invention also relates to a shuttle plasmid vector comprising: an adenoviral portion and a plasmid portion, wherein said adenovirus portion comprises: a) a replication defective adenovirus genome which does not have a functional E1 gene; and b) a gene expression cassette comprising: a nucleic acid encoding an HIV gag protein, wherein the nucleic acid is codon optimized for expression in a human host; a heterologous promoter operably linked to the nucleic acid encoding the gag protein; and a transcription terminator.

Other aspects of this invention include a host cell comprising the adenoviral vaccine vectors and/or the shuttle plasmid vectors, methods of producing the vectors comprising introducing the adenoviral vaccine vector into a host cell which expresses adenoviral E1 protein, and harvesting the resultant adenoviral vaccine vectors.

Another aspect of this invention is a method of generating a cellular immune response against an HIV protein in an individual comprising administering to the individual an adenovirus vaccine vector comprising:

a) a replication defective adenoviral vector, wherein the adenoviral vector does not have a functional E1 gene, and b) a gene expression cassette comprising: i) a nucleic acid encoding, an HIV gag protein, wherein the nucleic acid is codon optimized for expression in a human host; ii) a heterologous promoter operatively linked to the nucleic acid encoding the gag protein; and iii) a transcription terminator.

In some embodiments of this invention, the individual is given more than one administration of adenovirus vaccine vector, and it may be given in a regiment accompanied by the administration of a plasmid vaccine. The plasmid vaccine comprises a plasmid encoding a codon-optimized gag protein, a heterologous promoter operably linked to the gag protein nucleic acids, and a transcription terminator. There may be a predetermined minimum amount of time separating the, administrations. The individual can be given a first dose of plasmid vaccine, and then a second dose of plasmid vaccine. Alternatively, the individual may be given a first dose of adenovirus vaccine vector, and then a second dose of adenoviral vaccine vector. In other embodiments, the plasmid vaccine is administered first, followed after a time by administration of the adenovirus vector vaccine. Conversely, the adenovirus vaccine vector may be administered first, followed by administration of plasmid vaccine after a time. In these embodiments, an individual may be given multiple doses of the same adenovirus serotype in either viral vector or plasmid form, or the virus may be of differing serotypes.

BRIEF DESCRIPTION OF THE FIGURES

FIGS. 4A, B, and C are the first group of monkeys, D, E, and F are the second, and G, H, and I are the third group. Each represents specific killing responses of each monkey receiving the indicated treatment. The abscissa axis shows the effector/target (E/T) ratios of cultured T cells and B cells employed in this assay, while the ordinate axis shows specific lysis values obtained for each sample. Specific lysis values of at least 10% difference between curves±gag peptide antigen are generally considered significant. The square symbols represent target cells treated with DMSO alone at the same concentration as samples containing peptides while the circles, triangles, and diamonds represent target cells treated with partial (F, G) or complete (H) gag peptide pools, respectively.

FIG. 6 is the nucleic acid sequence (SEQ.ID.NO.1) of the optimized human HIV-1 gag open reading frame.

FIG. 8 is the nucleic acid sequence of the optimized tPA-gag open reading frame.

FIG. 9 show the longevity (69 weeks after final boost) of cellular immune responses in rhesus monkeys immunized with Ad5FLgag FIG. 10 shows CMI repsonses prior to and subsequent to a week 24 boost with Ad5-FLgag (SFC/$10^6$ cells via ELIspot)

FIG. 11 shows long term CMI responses for an HIV gag DNA vaccine (0, 4 and 8 weeks) and Ad5FLgag (single prime at T=0) which were boosted. with $10^7$ particles of Ad5FLgag (SFC/$10^6$ cells via ELIspot).

FIGS. 13A–E shows the longitudinal p11 C-specific tetramer staining results for all Mamu-A*01 monkeys up to one week before challenge. These data are presented as a percentage of the $CD3^+CD8^+$positive T cell population. Arrows indicate time of innoculations. (A) SIV gag DNA; (B) MVA-SIV gag; (C) SIV gag DNA+alum/MPL; (D) Ad5-SIV gag; and (E) SIV gag DNA+CRL1005.

FIGS. 14A–F show post challenge longitudinal results for peripheral p11C-specific tetramer staining for each group, as follows: (A) SIV gag DNA; (B) SIV gag DNA+CRL1005; (C) SIV gag DNA+alum/MPL; (D) MVA-SIV gag; (E) AdS-SIV gag; and, (F) naïve animals.

FIGS. 15A–L shows post-challenge CD4 T cell counts (A, C, E, G, and I) and plasma viral load (B, D, F. H, J, L) for each group, as follows: (A, B) SIV gag DNA; (C,D) SIV gag DNA +CRL1005; (E, F) SIV gag DNA +alum/MPL; (G, H) MVA-SIV gag; (I, J) Ad5-SIV gag; and, (K, L) naïve animals.

Figure 1:
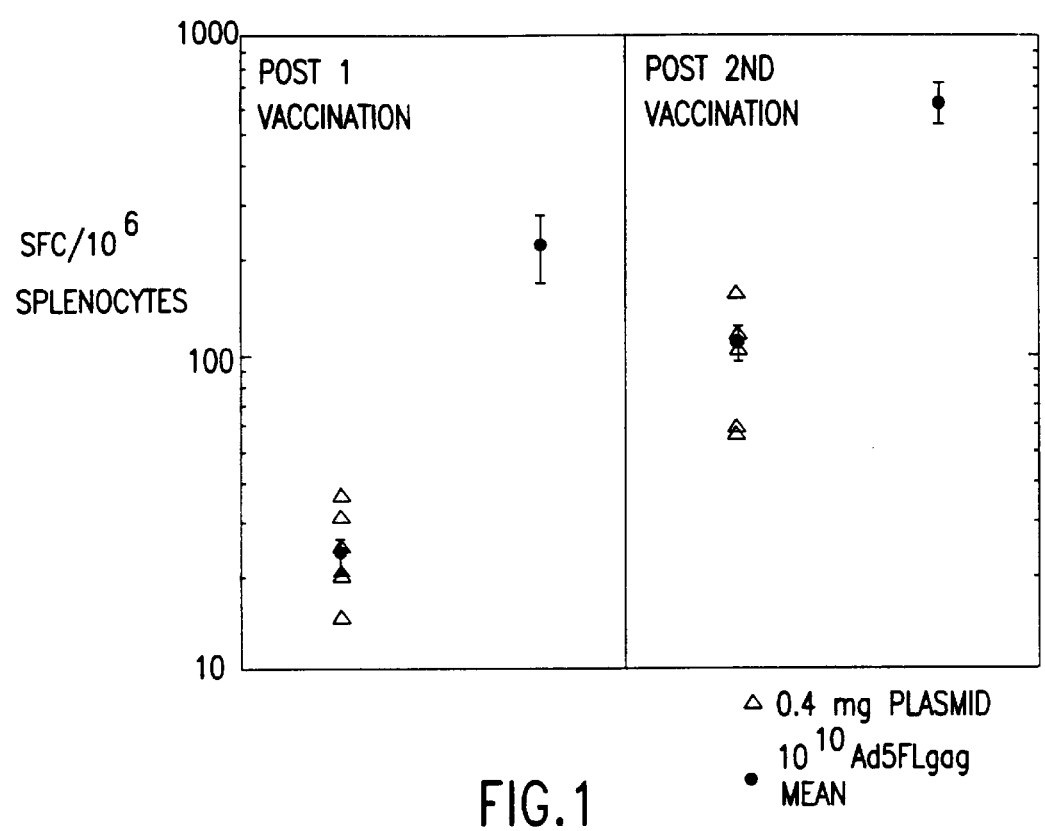
FIG. 1 is a graph showing the number of gag peptide-specific interferon-gamma secreting splenocytes ($\times 10^6$) from rats which were immunized with gag plasmid or Ad5FLgag.

As used throughout the specification and claims, the following definitions and abbreviations are used:

In general, adenoviral constructs, gene constructs are named by reference to the genes contained therein, such as below:

"tPAgag" refers to a fusion between the leader sequence of the tissue plasminogen activator leader sequence and an optimized HIV gag gene. "Ad5-tPAgag" refers to an adenovirus serotype 5 replication deficient virus which carries an expression cassette which comprises a tissue plasminogen activator leader sequence fused to a codon-optimized gag gene which is under the control of the CMV promoter and contains Intron A.

"Fl" refers to a full length gene. "Flgag" refers to the full-length optimized gag gene. "Ad5-Flgag" refers to an adenovirus serotype 5 replication deficient virus which carries an expression cassette which comprises a full length optimized gag gene under the control of the CMV promoter and contains Intron A.

"FG Adenovirus" means a First Generation adenovirus, i.e. a replication deficient adenovirus which has either a non-functional or deleted E1 region, and optionally a non-functional or deleted E3 region.

"Promoter" means a recognition site on a DNA strand to which an RNA polymerase binds. The promoter forms an initiation complex with RNA polymerase to initiate and drive transcriptional activity. The complex can be modified by activating sequences such as enhancers or inhibiting sequences such as silencers.

"Leader" means a DNA sequence at the 5' end of a structural gene which is transcribed along with the gene. This usually results a protein having an N-terminal peptide extension, often referred to as a pro-sequences.

"Intron" as used herein refers to a section of DNA occurring in the middle of a gene which does not code for an amino acid in the gene product. The precursor RNA of the intron is excised and is therefore not transcribed into mRNA not translated into protein.

"Cassette" refers to the a nucleic acid sequence which is to be expressed, along with its transcription and translational control sequences. By changing the cassette, a vector can express a different sequence.

It has been found according to this invention that first generation adenoviral vectors carrying a codon-optimized HIV gag gene regulated with a strong heterologous promoter can be used as human anti-HIV vaccines, and are capable of inducing immune responses.

The adenoviral vector which makes up the backbone of the vaccine construct of this invention is preferably a "first generation" adenoviral vector. This group of adenoviral vectors is known in the art, and these viruses are characterized by being replication-defective. They typically have a deleted or inactivated E1 gene region, and preferably additionally have a deleted or inactivated E3 gene region. In a preferred embodiment of this invention, the first generation replication incompetent adenovirus vector used is a serotype 5 adenovirus containing deletions in E1 (Ad5 base pairs 342–3523) and E3 (AdS base pairs 28133 to 30818). For adenovirus 2 serotype, the E1 deletions are preferably bp 559–3503 and the E3 deletions are preferably 28,812–29,773. (Genbank gb:J01917). Those of skill in the art can easily determine the equivalent sequences for other serotypes, such as serotypes 4, 12, 6, 17, 24, 33, 42, 31, 16.

Adenoviral serotypes 2 and 5, particularly 5 are preferred for use in this invention, since at this point in time, more is known about these serotypes generally than other serotypes, and their complete DNA sequences are known. The prototype serotype 5 adenovirus has been completely sequenced (Chroboczek et al, 1992 *J. Virology* 186:280, which is hereby incorporated by reference.) They also belong to the subgroup C adenoviruses, which are not associated with human or rodent malignancies. However, it is envisioned that any adenovirus serotype can be used in this invention, including non-human ones, as deletion of E1 genes should render all adenoviruses non-tumorogenic. Also it may be advantageous to use a serotype which has less prevalence in the wild, as patients are less likely to have previous exposure (and less pre-existing antibodies) to a rarer serotype.

The adenoviral vectors can be constructed using known techniques, such as those reviewed in Hitt et al, 1997 "Human Adenovirus Vectors for Gene Transfer into Mammalian Cells" *Advances in Pharmacology* 40:137–206, which is hereby incorporated by reference.

In constructing the adenoviral vectors of this invention, it is often convenient to insert them in to a plasmid or shuttle vector. These techniques are known and described in Hitt et al supra. This invention specifically includes both the adenovirus and the adenovirus when inserted into a shuttle plasmid.

Viral vectors can be propagated in various E1 complementing cell lines, including the known cell lines 293 and PER.C6. Both these cell lines express the adenoviral E1 gene product. PER.C6 is described in WO 97/00326, published Jan. 3, 1997, which is hereby incorporated by reference. It is a primary human retinoblast cell line transduced with an E1 gene segment that complements the production of replication deficient (FG) adenovirus, but is designed to prevent generation of replication competent adenovirus by homologous recombination. 293 cells are described in Graham et al 1977 J. Gen. Virol 36:59–72, which is hereby incorporated by reference.

The HIV gag gene selected to be expressed is of importance to the invention. Sequences for many genes of many HIV strains are publicly available in GENBANK and primary, field isolates of HIV are available from the National Institute of Allergy and Infectious Diseases (NIAID) which has contracted with Quality Biological (Gaithersburg, Md.) to make these strains available. Strains are also available from the World Health Organization (WHO), Geneva Switzerland. In a preferred embodiment of this invention, the gag gene is from an HIV-1 strain (CAM-1; Myers et al, eds. "Human Retroviruses and AIDS: 1995, IIA3-IIA19, which is incorporated by reference). This gene closely resembles the consensus amino acid sequence for the dade B (North American/European) sequence.

Regardless of the HIV gene chosen for expression, the sequence should be "optimized" for expression in a human cellular environment. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist variable natural hierarchy or "preference" for certain codons in certain types of cells. As one example, the amino acid leucine is specified by any of six DNA codons including CTA, CTC, CTG, CTT, TTA, and TTG (which correspond, respectively, to the MRNA codons, CUA, CUC, CUG, CUU, UUA and UUG). Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an *E. coli* host will depend to some extent on the frequency of codon use. For example, a gene rich in TTA codons will in all probability be poorly expressed in *E. coli*, whereas a CTG rich gene will probably highly express the polypeptide. Similarly, when yeast cells are the projected transformation host cells for expression of a leucine-rich polypeptide, a preferred codon for use in an inserted DNA would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide a preferred form of foreign genetic material for practice of recombinant DNA techniques. Thus, one aspect of this invention is an adenovirus vector which specifically includes a gag gene which is codon optimized for expression in a human cellular environment.

The diversity of function that typifies eukaryotic cells depends upon the structural differentiation of their membrane boundaries. To generate and maintain these structures, proteins must be transported from their site of synthesis in the endoplasmic reticulum to predetermined destinations throughout the cell. This requires that the trafficking proteins display sorting signals that are recognized by the molecular machinery responsible for route selection located at the access points to the main trafficking pathways. Sorting decisions for most proteins need to be made only once as they traverse their biosynthetic pathways since their final destination, the cellular location at which they perform their function, becomes their permanent residence.

Maintenance of intracellular integrity depends in part on the selective sorting and accurate transport of proteins to their correct destinations. Over the past few years the dissection of the molecular machinery for targeting and localization of proteins has been studied vigorously. Defined sequence motifs have been identified on proteins which can act as "address labels". Leader or signal peptides such as that from the tissue-specific plasminogen activator protein, tPA, serve to transport a protein into the cellular secretory pathway through the endoplasmic reticulum and golgi apparatus. A number of sorting signals have been found associated with the cytoplasmic domains of membrane proteins such as di-Leucine amino acid motifs or tyrosine-based sequences that can direct proteins to lysosomal compartments. For HIV, transport and extrusion from the cell of viral particles depend upon myristoylation of glycine residue number two at the amino terminus of gag. In some embodiments of the optimized gag gene, the tPA leader sequence has been attached 5' to the structural gene sequence.

The optimized gag gene is incorporated into an expression cassette. The cassette contains a transcriptional promoter recognized by an eukaryotic RNA polymerase; and a transcriptional terminator at the end of the gag gene coding sequence. In a preferred embodiment, the promoter is a "strong" or "efficient" promoter. An example of a strong promoter is the immediate early human cytomegalovirus promoter (Chapman et al, 1991 Nucl. Acids Res 19:3979–3986, which is incorporated by reference) with the intron A sequence (CMV-intA), although those skilled in the art will recognize that any of a number of other known promoters, such as the strong immunoglobulin, or other eukaryotic gene promoters may be used, including the EF1 alpha promoter, the murine CMV promoter, Rous sarcoma virus (RSV) promoter, SV40 early/late promoters and the beta-actin promoter. A preferred transcriptional terminator is the bovine growth hormone terminator. The combination of CMVintA-BGH terminator is particularly preferred although other promoter/terminator combinations in the context of FG adenovirus may also be used.

To assist in preparation of the polynucleotides in prokaryotic cells, a shuttle vector version of the adenovirus vector is often prepared. The shuttle vector contains an adenoviral portion and a plasmid portion. The adenoviral portion is essentially the same as the adenovirus vector discussed supra, containing adenoviral sequences (with non-functional or deleted E1 and E3 regions) and the gag expression cassette, flanked by convenient restriction sites. The plasmid portion of the shuttle vector often contains an antibiotic resistance marker under transcriptional control of a prokaryotic promoter so that expression of the antibiotic does not occur in eukaryotic cells. Ampicillin resistance genes, neomycin resistance genes and other pharmaceutically acceptable antibiotic resistance markers may be used. To aid in the high level production of the polynucleotide by fermentation in prokaryotic organisms, it is advantageous for the shuttle vector to contain a prokaryotic origin of replication and be of high copy number. A number of commercially available prokaryotic cloning vectors provide these benefits. It is desirable to remove non-essential DNA sequences. It is also desirable that the vectors not be able to replicate in eukaryotic cells. This minimizes the risk of integration of polynucleotide vaccine sequences into the recipients' genome. Tissue-specific promoters or enhancers may be used whenever it is desirable to limit expression of the polynucleotide to a particular tissue type.

In one embodiment of this invention, the shuttle plasmid used is pAD.CMVI-FLHIVgag, was made using homologous recombination techniques. For clinical use, the shuttle vector was rescued into virus in PER.C6 cells. To rescue, the shuttle plasmid was linearized by PacI restriction enzyme digestion and transfected into the PER.C6 cells using the calcium phosphate coprecipitate method. The plasmid in linear form is capable of replication after entering the PER.C6 cells and virus is produced. The infected cells and media were harvested after viral replication was complete.

Standard techniques of molecular biology for preparing and purifying DNA constructs enable the preparation of the DNA immunogens of this invention.

To ensure a clonal virus population a method of clonal purification was used for clinical material. The virus obtained from transfection of the PER.C6 cells was serially diluted to extinction using 2-fold dilutions. The dilutions were then used to infect PER.C6 cells in 96 well plates using 24 wells for each solution At the end of a 14-day incubation period the wells were scored positive or negative using adenovirus specific PCR and gag ELISA. Virus positive wells at the highest dilutions were selected for expansion. The selected well was the only positive well out of 24 wells plated at that dilution giving 98% assurance of clonality Verification of that endpoint had been reached in the dilution series, and that virus positive wells that had insufficient virus to be detected in the initial screening had not been missed, was obtained by subculturing the original 96 well plated two additional times and re-scoring them This confirmed the clonality of the selected well. The selected virus was designated AD5FLgag.

The adenoviral vaccine composition may contain physiologically acceptable components, such as buffer, normal saline or phosphate buffered saline, sucrose, other salts and polysorbate. One preferred formulation has: 2.5–10 mM TRIS buffer, preferably about 5 mM TRIS buffer; 25–100 mM NaCl, preferably about 75 mM NaCl; 2.5–10% sucrose, preferably about 5% sucrose; 0.01–2 mM $MgCl_2$; and 0.001%–0.01% polysorbate 80 (plant derived). The pH should range from about 7.0–9.0, preferably about 8.0. One skilled in the art will appreciate that other conventional vaccine excipients may also be used it make the formulation. The preferred formulation contains 5 mM TRIS, 75 mM NaCl, 5% sucrose, 1 mM $MgCl_{2,}$ $_{0.005}$% polysorbate 80 at pH 8.0 This has a pH and divalent cation composition which is near the optimum for AdS stability and minimizes the potential for adsorption of virus to a glass surface. It does not cause tissue irritation upon intramuscular injection. It is preferably frozen until use.

The amount of adenoviral particles in the vaccine composition to be introduced into a vaccine recipient will depend on the strength of the transcriptional and translational promoters used and on the immunogenicity of the expressed gene product. In general, an immunologically or prophylactically effective dose of $1 \times 10^7$ to $1 \times 10^{12}$ particles and preferably about $1 \times 10^{10}$ to $1 \times 10^{10}$ particles is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided. Following vaccination with HIV adenoviral vector, boosting with a subsequent HIV adenoviral vector anchor plasmid may be desirable. Parenteral administration, such as intravenous, intramuscular, subcutaneous or other means of administration of interleukin-12 protein, concurrently with or subsequent to parenteral introduction of the vaccine compositions of this invention is also advantageous.

Another aspect of this invention is the administration of the adenoviral vector containing the optimized gag gene in a prime/boost regiment in conjunction with a plasmid DNA encoding gag. To distinguish this plasmid from the adenoviral-containing shuttle plasmids used in the construction of an adenovirus vector, this plasmid will be referred to as a "vaccine plasmid". The preferred vaccine plasmids to use in this administration protocol are disclosed in pending U.S. patent application Ser. No. 09/017,981, filed Feb. 3, 1998 and WO98/34640, published Aug. 13, 1998, both of which are hereby incorporated by reference. Briefly, the preferred vaccine plasmid is designated V1Jns-FL-gag, which expresses the same codon-optimized gag gene as the adenoviral vectors of this invention. The vaccine plasmid backbone, designated V1Jns contains the CMV immediate-early (IE) promoter and intron A, a bovine growth hormone-derived polyadenylation and transcriptional termination sequence as the gene expression regulatory elements, and a minimal pUC backbone (Montgomery et al, 1993 *DNA Cell Biol.* 12:777–783. The pUC sequence permits high levels of plasmid production in *E. coli* and has a neomycin resistance gene in place of an ampicillin resistance gene to provide selected growth in the presence of kanamycin. Those of skill in the art, however, will recognized that alternative vaccine plasmid vectors may be easily substituted for this specific construct, and this invention specifically envisions the use of alternative plasmid DNA vaccine vectors.

The adenoviral vector and/or vaccine plasmids of this invention polynucleotide may be unassociated with any proteins, adjuvants or other agents which impact on the recipients' immune system. In this case, it is desirable for the vector to be in a physiologically acceptable solution, such as, but not limited to, sterile saline or sterile buffered saline. Alternatively, the vector may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

The adenoviral vaccines of this invention may be administered alone, or may be part of a prime and boost administration regimen. A mixed modality priming and booster inoculation scheme will result in an enhanced immune response, particularly is pre-existing anti-vector immune responses are present. This one aspect of this invention is a method of priming a subject with the plasmid vaccine by administering the plasmid vaccine at least one time, allowing a predetermined length of time to pass, and then boosting by administering the adenoviral vaccine. Multiple primings typically, 1–4, are usually employed, although more may be used. The length of time between priming and boost may typically vary from about four months to a year, but other time frames may be used. In experiments with rhesus monkeys, the animals were primed four rimes with plasmid vaccines, then were boosted 4 months later with the adenoviral vaccine. Their cellular immune response was notably higher than that of animals which had only received adenoviral vaccine. The use of a priming regimen may be particularly preferred in situations where a person has a pre-existing anti-adenovirus immune response.

This invention also includes a prime and boost regimen wherein a first adenoviral vector is administered, then a booster dose is given. The booster dose may be repeated at selected time intervals.

A large body of human and animal data supports the importance of cellular immune responses, especially CTL in controlling (or eliminating) HIV infection. In humans, very high levels of CTL develop following primary infection and correlate with the control of viremia. Several small groups of individuals have been described who are repeatedly exposed to HIV by remain uninfected; CTL has been noted in several of these cohorts. In the SIV model of HIV infection, CTL similarly develops following primary infection, and it has been demonstrated that addition of anti-CD8 monoclonal antibody abrogated this control of infection and leads to disease progression. This invention uses adenoviral vaccines alone or in combination with plasmid vaccines to induce CTL. Cellular Immunity Assays for Pre-Clinical and Clinical Research Another aspect of this invention is an assay which measures the elicitation of HIV-1 protein, including gag-specific cellular immunity, particularly cytotoxic T-lymphocyte (CTL) responses. The "ELIspot" and cytotoxicity assays, discussed herein, measure HIV antigen-specific CD8+ and CD4+T lymphocyte responses and can be used for a variety of mammals, such as humans, rhesus monkeys, mice, and rats.

The ELIspot assay provides a quantitative determination of HIV-specific T lymphocyte responses. PMBC cells are cultured in tissue culture microtiter plates. An HIV-1 gag peptide pool that encompasses the entire 500 amino acid open reading frame of gag (50 overlapping 20 mer peptides) is added to the cells and one day later the number of cells producing gamma interferon (or another selected interferon) is measured. Gamma interferon was selected as the cytokine visualized in this assay (using species specific anti-gamma interferon monoclonal antibodies) because it is the most common, and one of the most abundant cytokines synthesized and secreted by activated T lymphocytes. For this assay, the number of spot forming cells (SPC) per million PBMCs is determined for samples in the presence and absence (media control) of peptide antigens. This assay may be set up to determine overall T lymphocyte responses (both CD8+ and CD4+) or for specific cell populations by prior depletion of either CD8+ or CD4+ T cells. In addition, ELIspot assays, or variations of it, can be used to determine which peptide epitopes are recognized by particular individuals.

A distinguishing effector function of T lymphocytes is the ability of subsets of this cell population to directly lyse cells exhibiting appropriate MHC-associated antigenic peptides. This cytotoxic activity is most often associated with CD8+ T lymphocytes but may also be exhibited by CD4+ T lymphocytes. We have optimized bulk culture CTL assays in which PBMC samples are infected with recombinant vaccinia viruses expressing antigens (e.g., gag) in vitro for approximately 14 days to provide antigen restimulation and expansion of memory T cells that are then tested for cytoxicity against autologous B cell lines treated either with peptide antigen pools. Specific cytotoxicity is measured compared to irrelevant antigen or excipient-treated B cell lines. The phenotype of responding T lymphocytes is determined by appropriate depletion of either CD8+ or CD4+ populations prior to the cytotoxicity assay. This assay is semi-quantitative and is the preferred means for determining whether CTL responses were elicited by the vaccine.

The following non-limiting Examples are presented to better illustrate the invention.

EXAMPLES

Example 1

Construction of Replication-Defective FG-Ad Expressing HIV Gag Antigen

Starting Vectors

Shuttle vector pHCMVIBGHpA1 contains Ad5 sequences from bp1 to bp 341 and bp 3534 to bp 5798 with a expression cassette containing human cytomegalovirus (HCMV) promoter plus intron A and bovine growth hormone polyadenylation signal.

The adenoviral backbone vector pAdE1-E3- (also named as phVad1) contains all Ad5 sequences except those nucleotides encompassing the E1 and E3 region.

Plasmid pV1JNStpaHIVgag contains tPA secretory signal sequence fused to the codon-optimized HIV gag nucleotides under the control of HCMV promoter plus intron A. It is described in pending U.S. patent application Ser. No. 09/017,981, filed Feb. 3, 1998 and WO98/34640, published Aug. 13, 1998, both of which are hereby incorporated by reference.

Plasmid pV1R-FLHIV gag (also named as pV1R-HIV gag-opt) contains codon-optimized full-length HIV gag under the control of the HCMV promoter plus intron A.

Construction of Ad5tpaHIV gag

1. Construction of adenoviral shuttle plasmid pA1-CMVI-tpaHIV gag containing tPAgag under the control of human CMV promoter and intron A.

The tPAgag insert was excised from pV1JNS-tPA gag by restriction enzymes PstI and XmaI, blunt-ended, and then cloned into EcoRV digested shuttle vector pHCMVIB-GHpA1. The orientation of the transgene and the construct were verified by PCR using the insert specific primers hCMV5'-4 (5'TAG CGG CGG AGC TTC TAC ATC 3' SEQ.ID.NO. 2) and Gag3'-1 (5' ACT GGG AGG AGG GGT CGT TGC 3' SEQ.ID.NO.3), restriction enzyme analysis (RcaI, SspBI), and DNA sequencing spanning from CMV promoter to the initiation of the gag.

2. Homologous recombination to generate shuttle plasmid form of recombinant adenoviral vector pAd-CMVI-tpaHIV gag containing tpaHIV gag expression cassette.

Shuttle plasmid pA1-CMVI-tpaHIV gag was digested with restriction enzymes BstZ17 and SgrA1 and then co-transformed into *E. coli* strain BJ5183 with linearized (ClaI digested) adenoviral backbone plasmid pAdE1-E3-. One colony was verified by PCR analysis. The vector was transformed to competent *E. coli* HB 101 for large quantity production of the plasmid.

3. Generation of recombinant adenovirus Ad.CMVI-tpaHIV gag in 293 cells.

The shuttle plasmid was linearized by restriction enzyme PacI and transfected to 293 cells using CaPO$_4$ method (InVitrogen kit). Ten days later, 10 plaques were picked and grown in 293 cells in 35-mm plates. PCR analysis of the adenoviral DNA indicated 10 out of 10 virus were positive for gag.

4. Evaluation of large scale recombinant adenovirus Ad.CMVI-tpaHIV gag

Clone No.9 was grown into large quantities through multiple rounds of amplification in 293 cells. One lot yielded of $1.7 \times 10^{12}$ particles and a second lot yielded $6.7 \times 10^{13}$ particles. The viral DNA was extracted by proteinase K digestion and confirmed by PCR and restriction enzyme (HindIII) analysis. The expression of tpaHIV gag was also verified by ELISA and Western blot analysis of the 293 or COS cells infected with the recombinant adenovirus. The recombinant adenovirus was used for evaluation in mice and rhesus monkeys.

Construction of Ad5.FHIV gag

1. Construction of adenoviral shuttle plasmid pA1-CMVI-FLHIV gag containing full length HIVgag under the control of human CMV promoter and intron A.

The FLHIV gag insert was excised from pV1R-FLHIV gag by restriction enzyme BglII and then cloned into BglII digested shuttle vector pHCMVIBGHpA1. The orientation and the construct were verified by PCR using the insert specific primers (hCMV5'-4 and Gag3'-1), restriction enzyme analysis, and DNA sequencing.

2. Homologous recombination to generate plasmid form of recombinant adenoviral vector pAd-CMVI-FLHIV gag containing FLHIV gag expression cassette.

Shuttle plasmid pA1-CMVI-FLHIV gag was digested with restriction enzymes BstZ17 and SgrA1 and then co-transformed into *E. coli* strain BJ5183 with linearized (ClaI digested) adenoviral backbone plasmid pAdE1-E3-. Colonies #6 and #7 were verified by PCR analysis. The vectors were transformed to competent *E. coli* HB101 for large quantity production of the plasmid. The plasmids were verified by HindIII digestion.

3. Generation of recombinant adenovirus Ad.CMVI-FLHIV gag in 293 cells.

The pAd plasmids were linearized by restriction enzyme PacI and transfected to 293 cells using Lipofectamine (BRL). Two weeks later, 6 viruses (#6-1.1, 6-1.2, 6-1.3, 7-1.1, 7-1.2, 7-1.3) were picked and grown in 293 cells in 35-mm plates. PCR analysis using the insert specific primers (hCMV5'-4 and Gag3'-1) of the adenoviral DNA verified the presence of HIV gag.

4. Evaluation of large scale recombinant adenovirus Ad. CMVI-FHIV gag

Virus clone #6-1 was grown into large quantities through multiple rounds of amplification in 293 cells. The viral DNA was extracted by proteinase K digestion and confirmed by PCR, restriction enzyme (HindIII, Bgl II, Bst E II, Xho I) analysis. A partial sequencing confirmed the junction between CMV promoter and the 5' end of HIV gag gene. The expression of FLHIV gag was also verified by ELISA and Western blot analysis of the 293 or COS cells infected with the recombinant adenovirus. The recombinant adenovirus was used for evaluation in mice and rhesus monkeys.

Construction of FG adenovirus FL gag.

The full-length (FL) humanized gag gene was ligated into an adenovirus-5 shuttle vector, pHCMVIBGHpA1, containing Ad5 sequences from bp 1 to bp 341 and bp 3534 to bp 5798 with a expression cassette containing human CMV promoter plus intron A and bovine growth hormone polyadenylation signal. The orientation was confirmed by restriction enzyme digestion analysis and DNA sequencing. Homologous recombination in *E. coli* was employed using the shuttle plasmid, pA1-CMVI-FLHIV gag, and adenoviral backbone plasmid, pAdE1-E3-, to generate a plasmid form of the recombinant adenovirus containing the expression regulatory elements and FL gag gene, pAd.CMVI-FHIV gag. Appropriate plasmid recombinants were confirmed by restriction enzyme digestion.

The pAd plasmid containing the gag expression cassette was linearized by restriction enzyme PacI and transfected to 293 cells (or PER.C6 cells for clinical development candidates) using Lipofectamine (BRL). Two weeks later, 6 viruses were picked and grown in 293 cells in 35-mm plates. PCR analysis using the insert specific primers (hCMV5'-4 and Gag3'-1) of the adenoviral DNA verified the presence of HIV gag. Virus clone #6-1 was grown into large quantities through multiple rounds of amplification in 293 cells. The viral DNA was extracted by proteinase K digestion and confirmed by PCR, restriction enzyme (HindIII, BglII, BstEII, XhoI) analysis. A partial sequencing confirmed the junction between CMV promoter and the 5' end of HIV gag gene. Restriction enzyme analysis demonstrated that the viral genome was stable over the course of these passages.

The expression of HIV gag was verified by ELISA and Western blot analysis of the 293 or COS cells infected with the recombinant adenovirus.

Example 2

Immunogenicity/Preclinical Efficacy

The "ELIspot" Assay

The ELIspot assay is a quantitative determination of IV-specific T lymphocyte responses by visualization of gamma interferon secreting cells in tissue culture microtiter plates one day following addition of an HIV-1 gag peptide pool that encompasses the entire 500 amino acid open reading frame of gag (50 overlapping 20 mer peptides) to PBMC samples. The number of spot forming cells (SPC) per million of PBMVs is determined for samples in the presence and absence (media control) of peptide antigens. The assay may be set up to determine overall T lymphocyte responses (both CD8+ and CD4+) or for specific cell populations by prior depletion of either CD8+ or CD4+ cells. In addition, the assay can be varied so as to determine which peptide epitopes are recognized by particular individuals.

Cytotoxic T Lymphocyte Assays

In this assay, PBMC samples are infected with recombinant vaccinia viruses expressing gag antigen in vitro for approximately 14 days to provide antigen restimulation and expansion of memory T cells. The cells are then tested for cytotoxicity against autologous B cell lines treated with peptide antigen pools. The phenotype of responding T lymphocytes is determined by appropriate depletion of either CD8+ or CD4+ cells.

A. Immune Responses to FG Adenovirus 5 FLgag Vaccine in Rodents

Adenovirus vectors coding for the gag antigen have consistently produced significantly stronger cellular immune responses than plasmid vectors in rodent species. Table 1 (below) shows ELIspot data from mice vaccinated with Ad5FLgag in comparison with plasmid DNA. Spleens from five mice were pooled and the number of gag peptide-specific interferon-gamma secreting cells was determined.

TABLE 1

Comparison of plasmid and adenovirus vaccination in mice

| | SFC/$10^6$ splenocytes | |
| --- | --- | --- |
| | Post 1st Vaccination | Post 2nd Vaccination |
| 10 µg plasmid | 68 | 324 |
| $10^5$ Ad5Flgag | 18 | 170 |
| $10^8$ Ad5Flgag | 530 | 5600 |

Similar enhancements in the cellular responses to gag were also seen in Fischer rats. FIG. 1 shows the ELIspot data from individual rats vaccinated with $10^{10}$ particles of adenovirus Ad5FLgag or with 0.4 mg FL gag plasmid. The mean response after one vaccination was 10-fold higher with adenovirus compared to plasmid. Both vaccines gave a boosted signal after a second vaccination, with the adenovirus vaccine signal 5-fold higher than the plasmid signal.

B. Immune Responses to FG Adenovirus 5 FL gag Vaccine in Rhesus Monkeys

Comparative in vivo expression of DNA vs. FGAd5 encoding a reporter gene.

Figure 2:
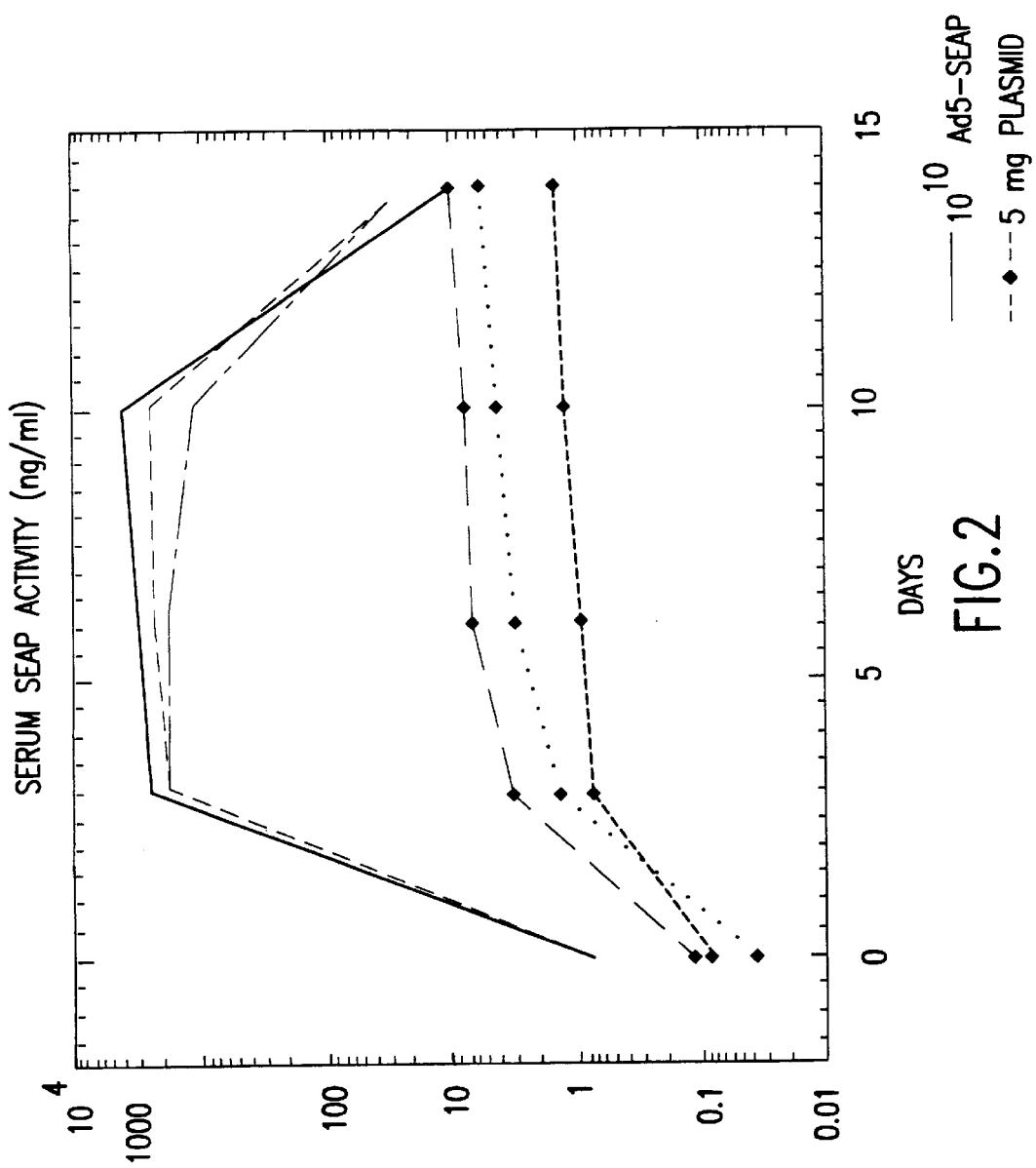
FIG. 2 shows serum SEAP (secreted alkaline phosphatase) expression levels in rhesus monkeys following injection with FG Ad5-SEAP or SEAP DNA constructs.

Adenovirus and plasmid vectors expressing the secreted alkaline phosphatase (SEAP) as a reporter gene were injected into rhesus monkeys to compare the levels of antigen produced by the two forms of vaccination as shown below. FIG. 2 shows that at the highest possible plasmid dose (5 mg), the antigen levels are 1,000-fold lower than the levels achieved using $10^{10}$ particles of adenovirus, a dose which is ten fold lower than the maximum proposed clinical dose.

FG adenovirus-5 FLgag vaccinations of rhesus monkeys. Three Rhesus monkeys were vaccinated at 0, 8, and 24 weeks with $10^{11}$ particles of FG adenovirus-5tPAgag, an adenoviral vector containing a form of the gag gene with a leader peptide from the tissue-specific plasminogen activator gene at the amino terminus. Data were collected starting at 20 weeks.

Figure 3A:
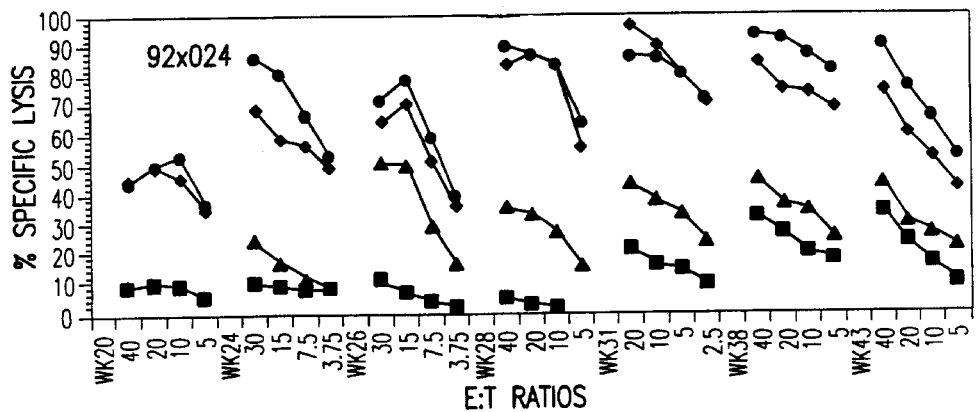
FIGS. 3A, 3B and 3C show anti-HIV gag cytotoxic T lymphocyte responses in three rhesus monkeys vaccinated with FG Ad5 tPAgag. Each panel represents the specific killing response of a particular monkeys (denoted as numbers 92×024 in FIG. 3A, 94×012 in FIG. 3B, and 94×025 in FIG. 3C) at various time points following immunization at 0, 8, and 24 weeks. The abscissa axis shows the effector/target (E/T) ratios of cultured T cells and B cells employed in this assay, while the ordinate axis shows specific lysis values obtained for each sample. Specific lysis values of at least 10% difference between curves±gag peptide antigen are generally considered significant. The square symbols represent target cells treated with an irrelevant influenza peptide antigen while the circles, triangles, and diamonds represent target cells treated with partial or complete gag peptide pools, respectively.
Figure 3B:
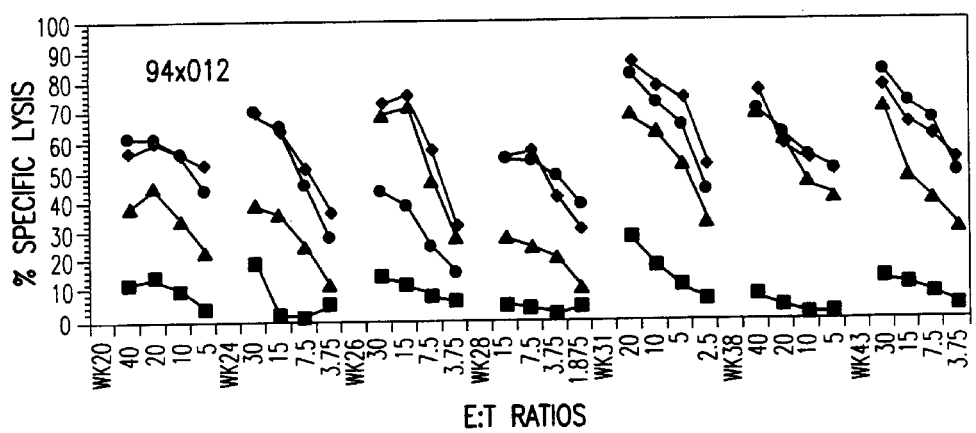
Figure 3C:
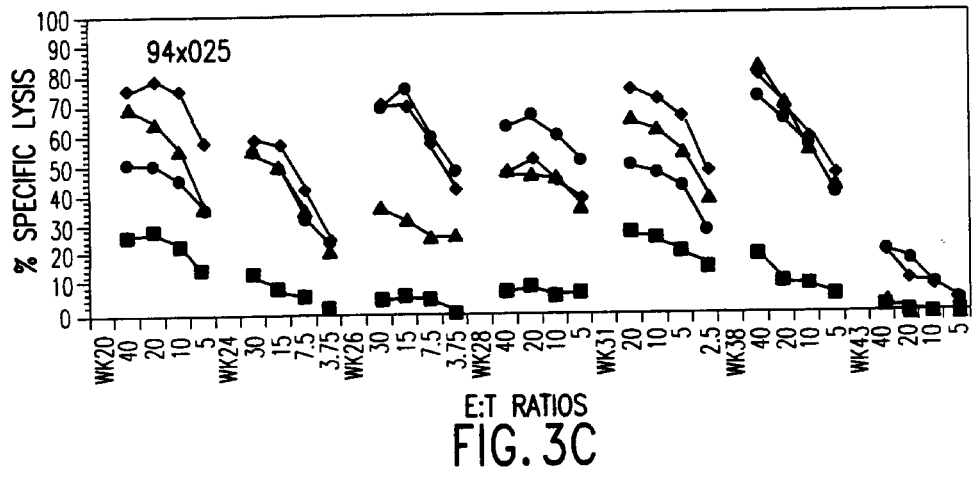
Figure 4A:
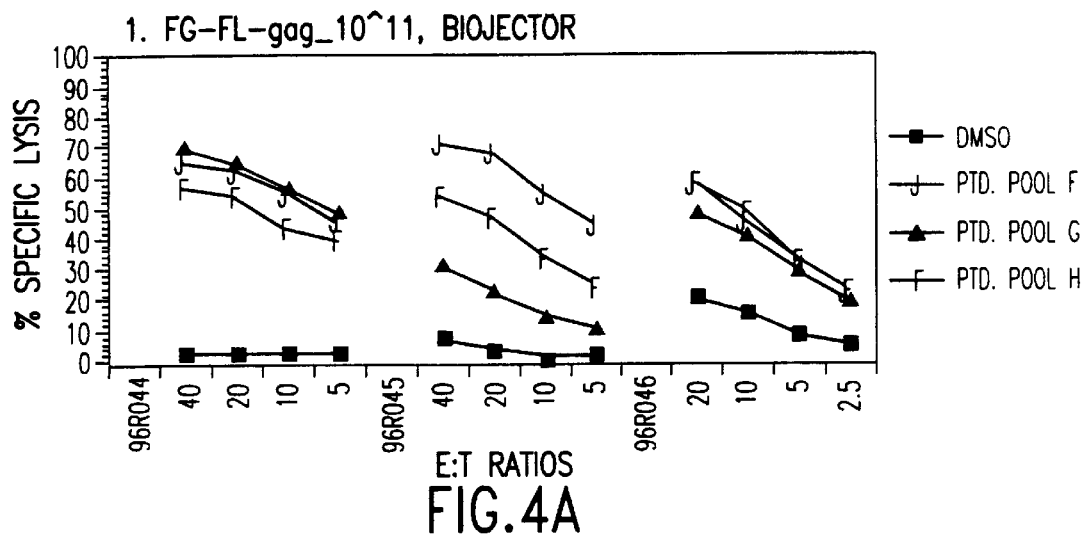
FIGS. 4A–H show anti-HIV gag cytotoxic T lymphocyte responses in rhesus monkeys vaccinated with FG Ad5FLgag.
Figure 4B:
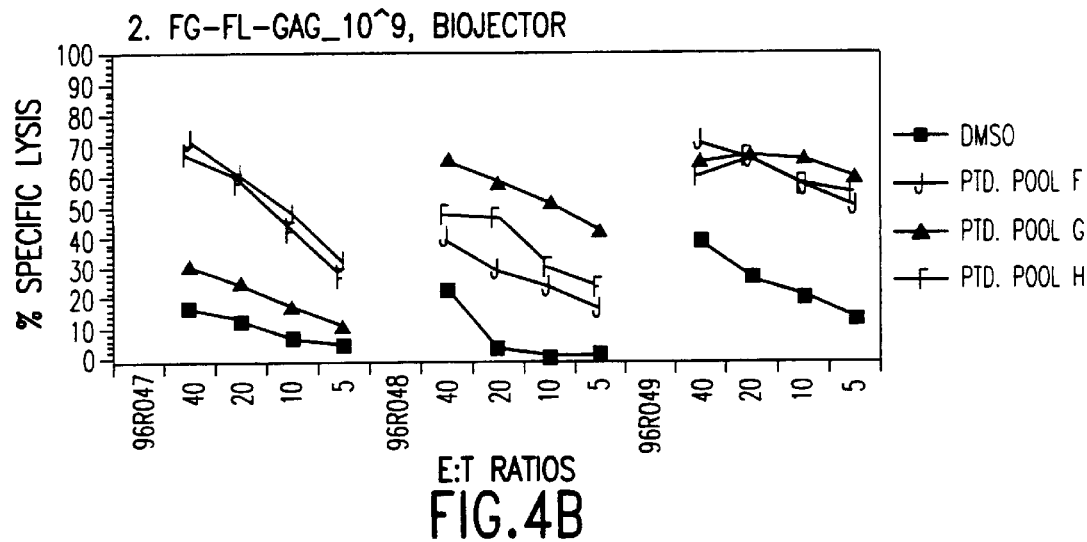
Figure 4C:
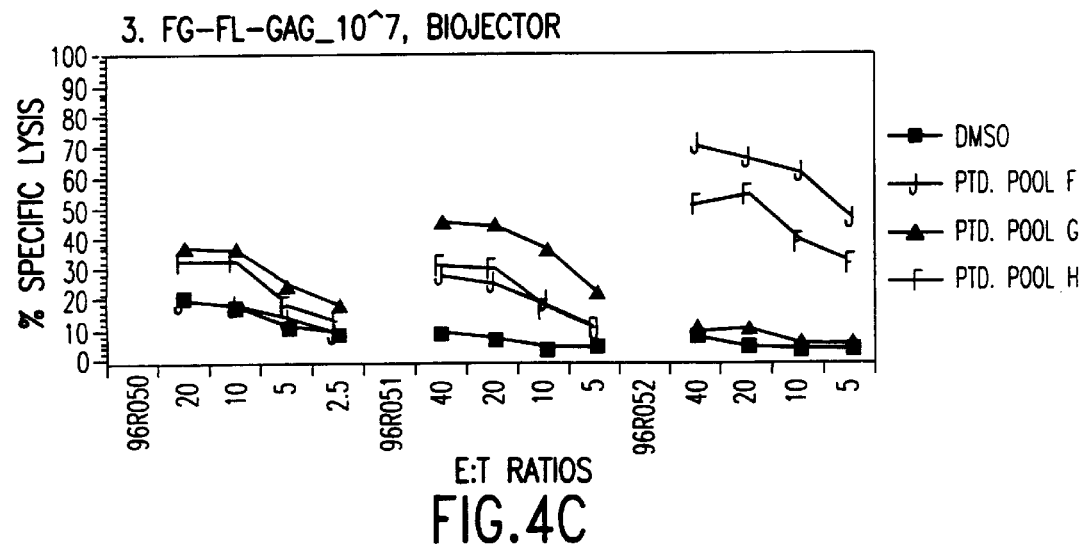
Figure 4D:
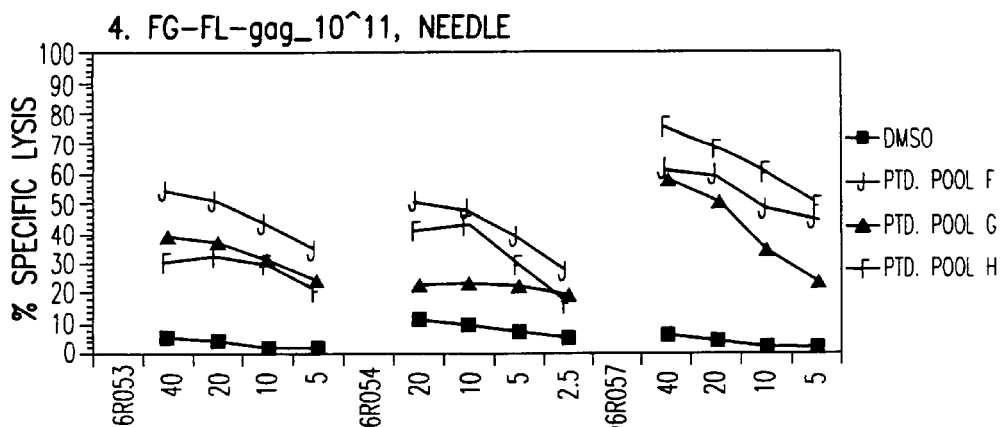
Figure 4E:
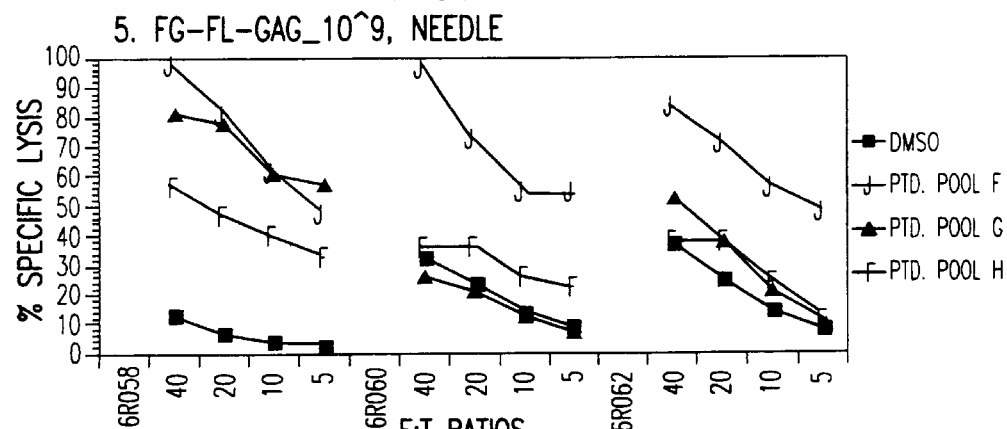
Figure 4F:
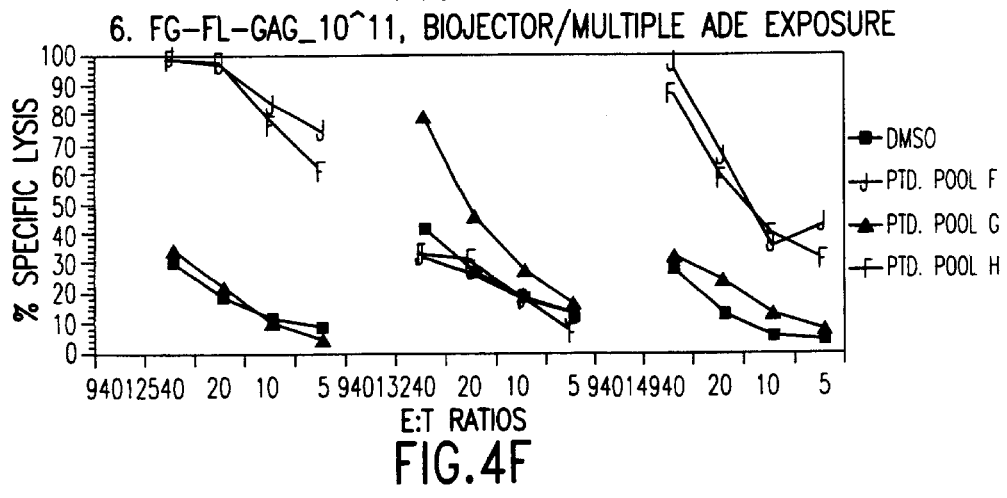
Figure 4G:
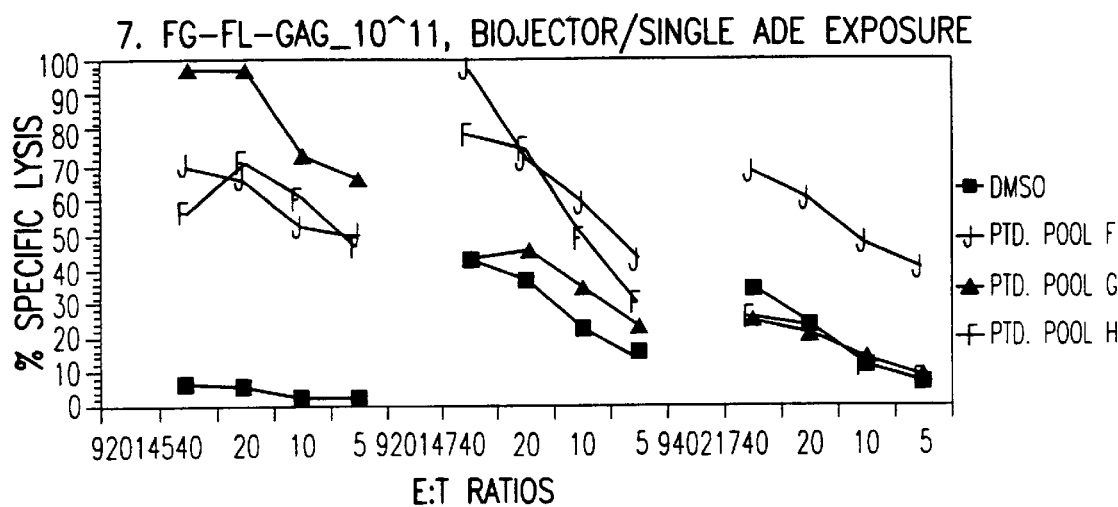
Figure 4H:
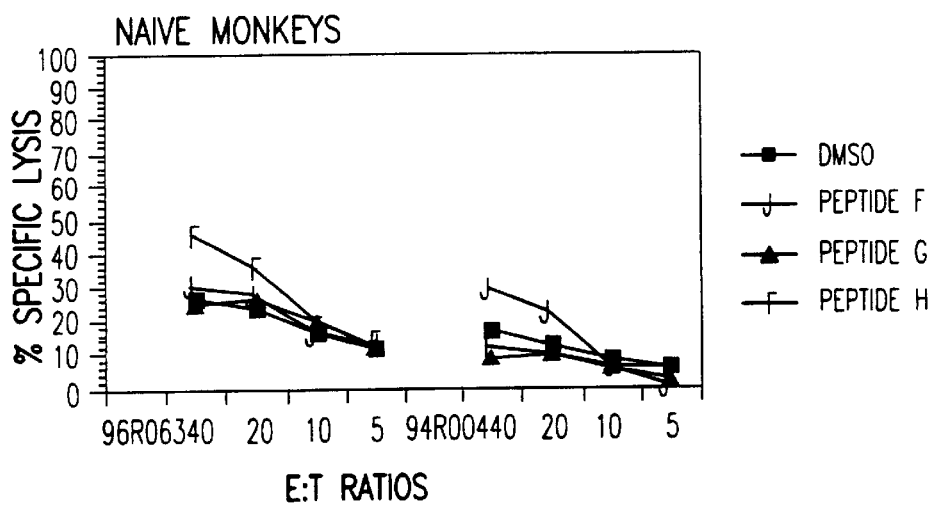
Figure 5A:
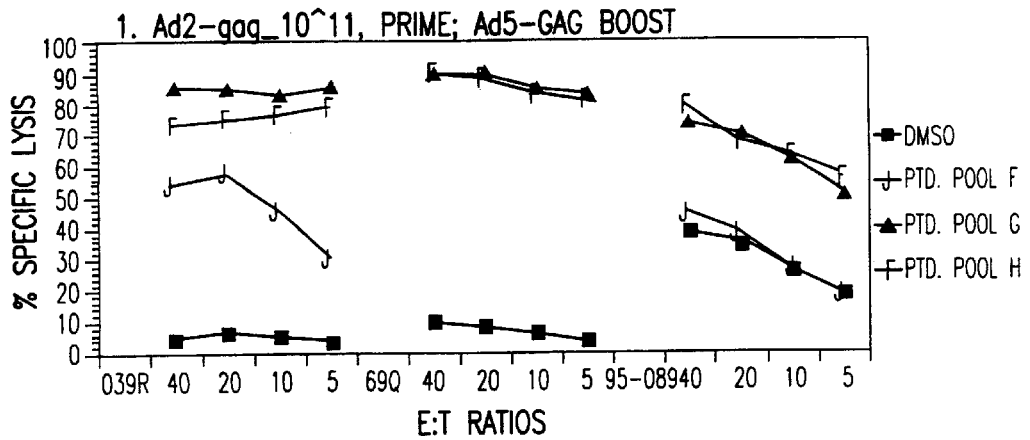
FIGS. 5A–H show anti-HIV gag cytotoxic T lymphocyte responses in rhesus monkeys vaccinated with Ad2Flgag priming, followed by either Ad2Flgag or Ad5Flgag boosting. Each panel (FIGS. 5A–G) represents specific killing responses of a group of three monkeys receiving the indicated treatment. The last panel (FIG. 5H) shows responses from two naïve monkeys that were not vaccinated. The abscissa axis shows the effector/target (E/T) ratios of cultured T cells and B cells employed in this assay, while the ordinate axis shows specific lysis values obtained for each sample. Specific lysis values of at least 10% difference between curves +gag peptide antigen are generally considered significant.
Figure 5B:
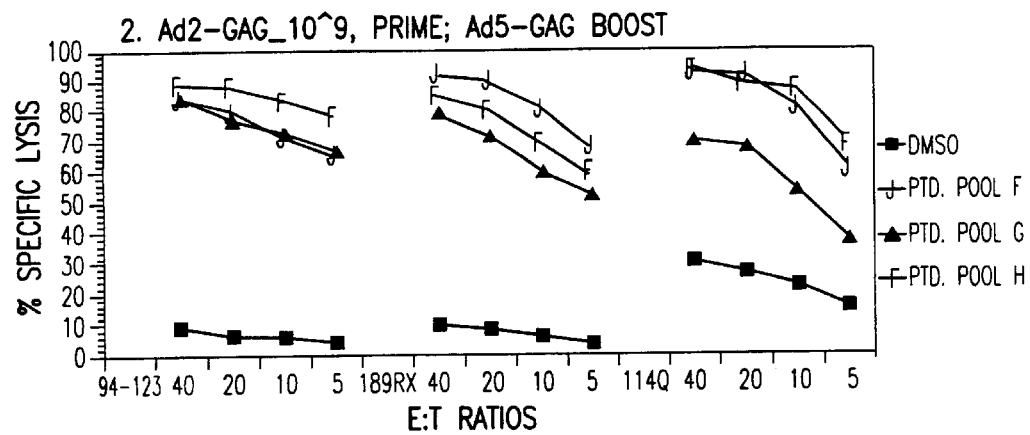
Figure 5C:
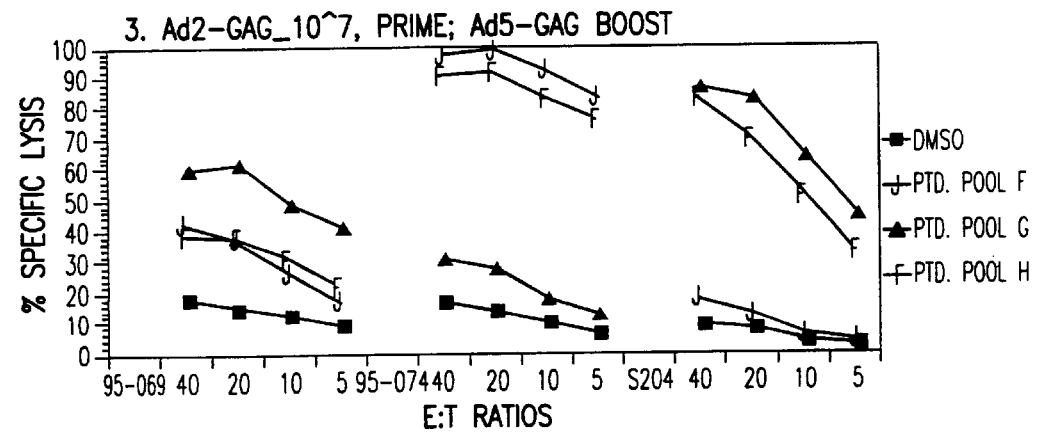
Figure 5D:
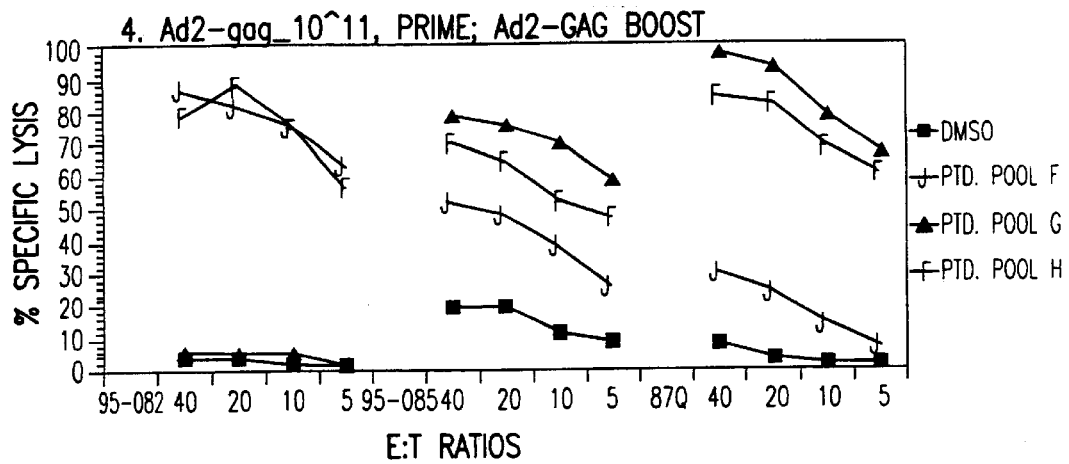
Figure 5E:
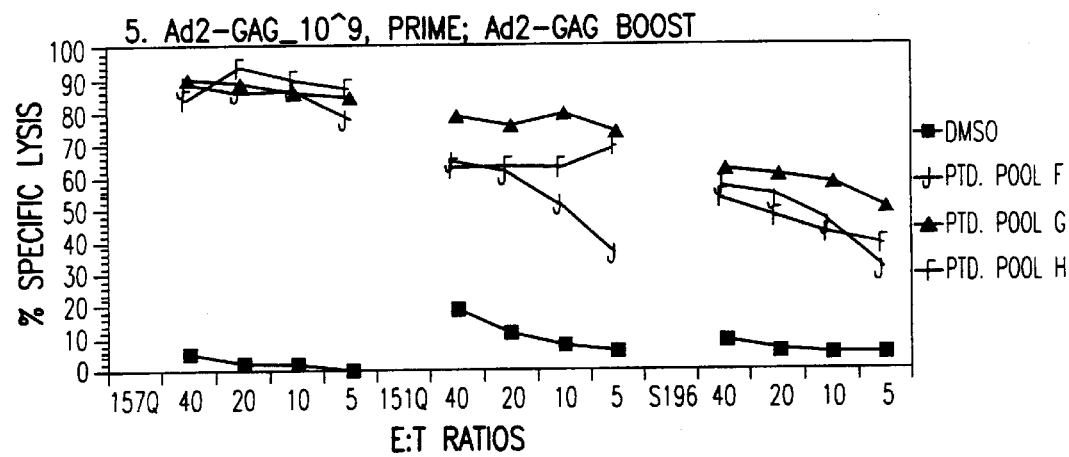
Figure 5F:
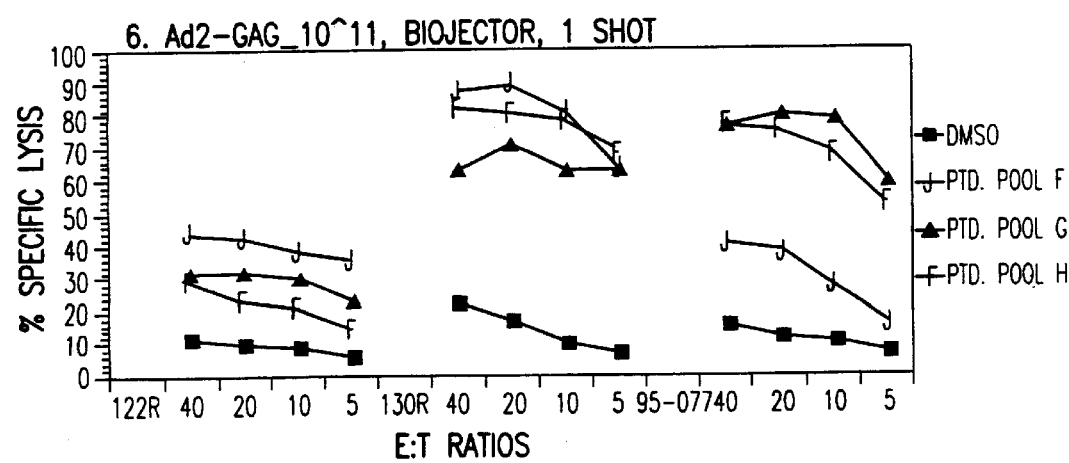
Figure 5G:
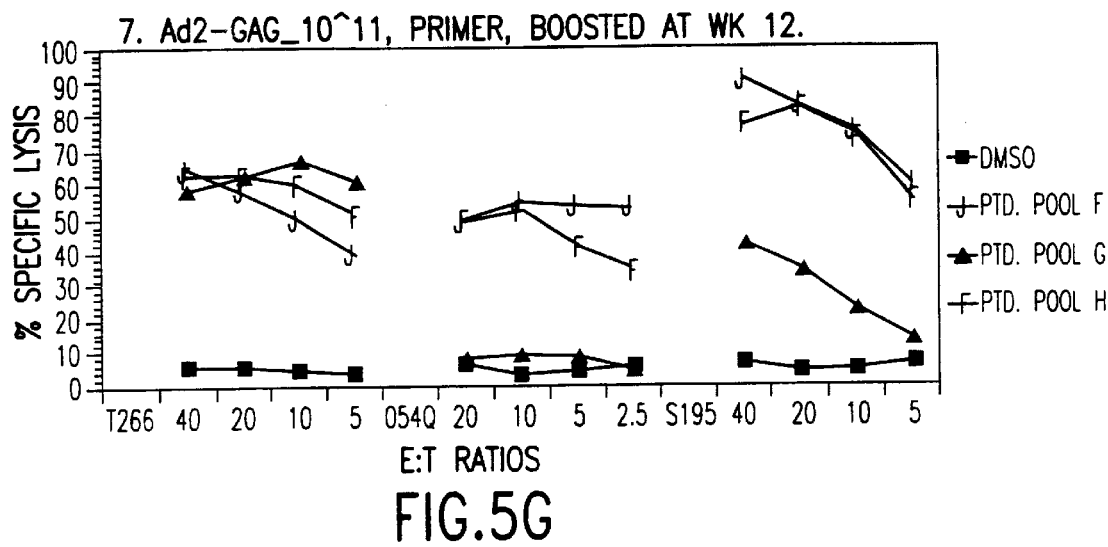
Figure 5H:
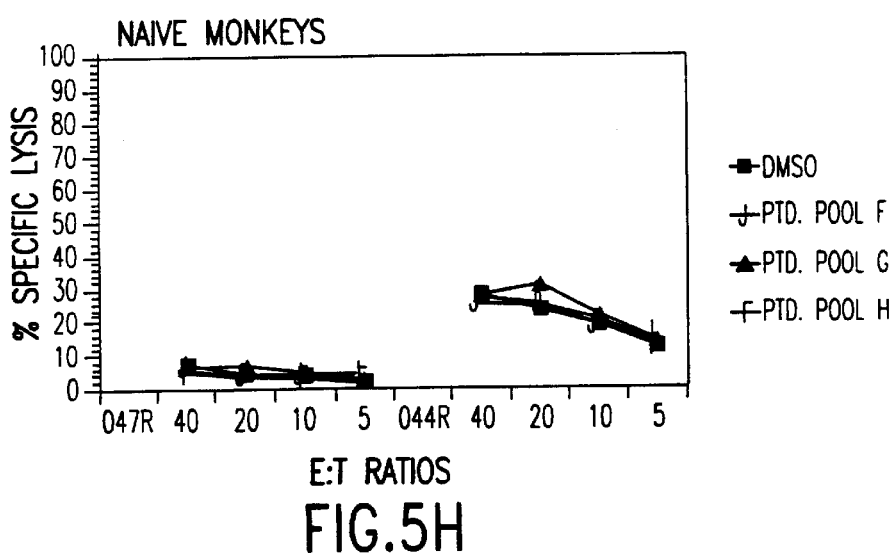
Figure 7A:
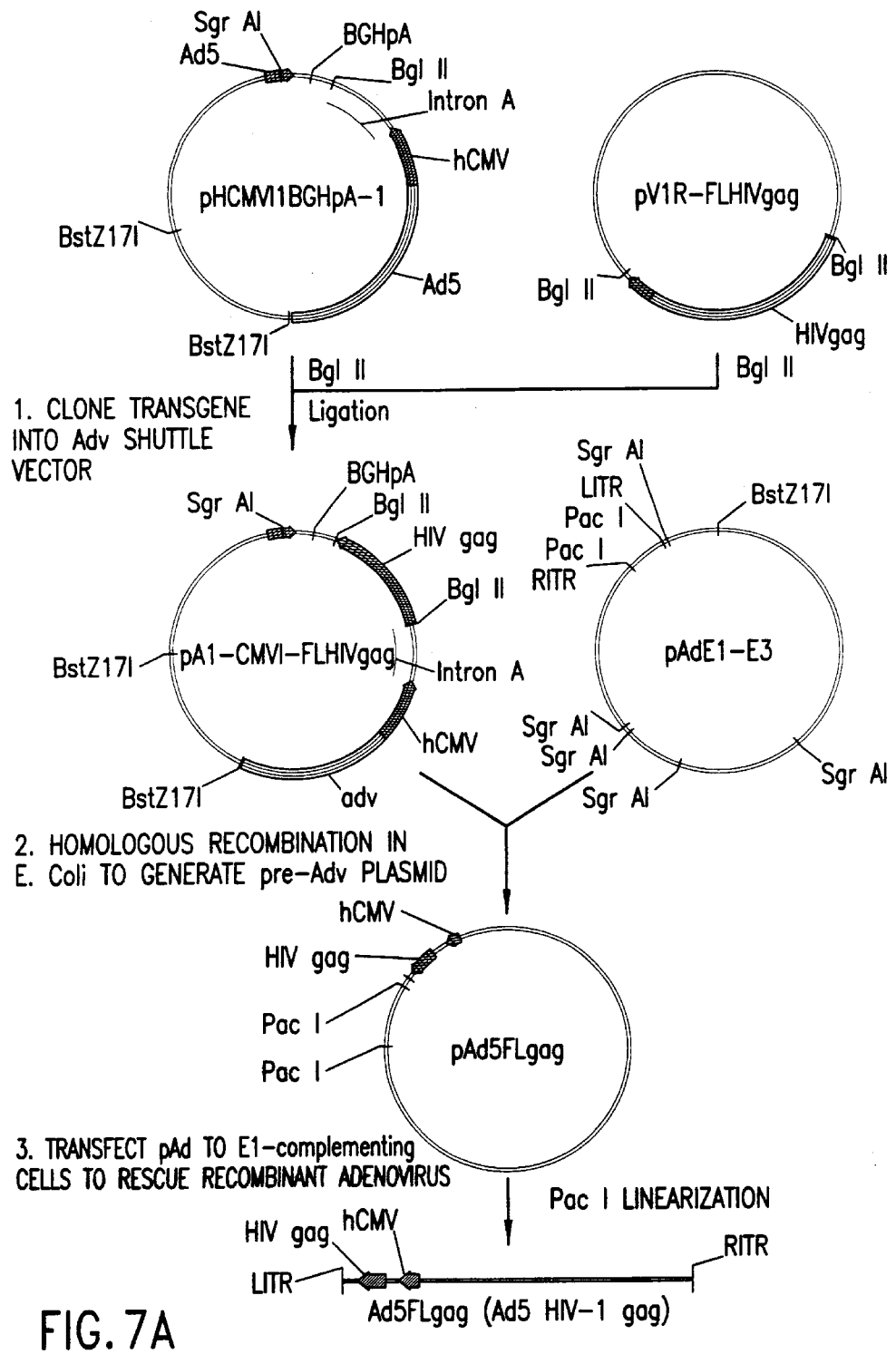
FIG. 7A shows construction of the adenovirus carrying codon-optimized gag.
Figure 7B:
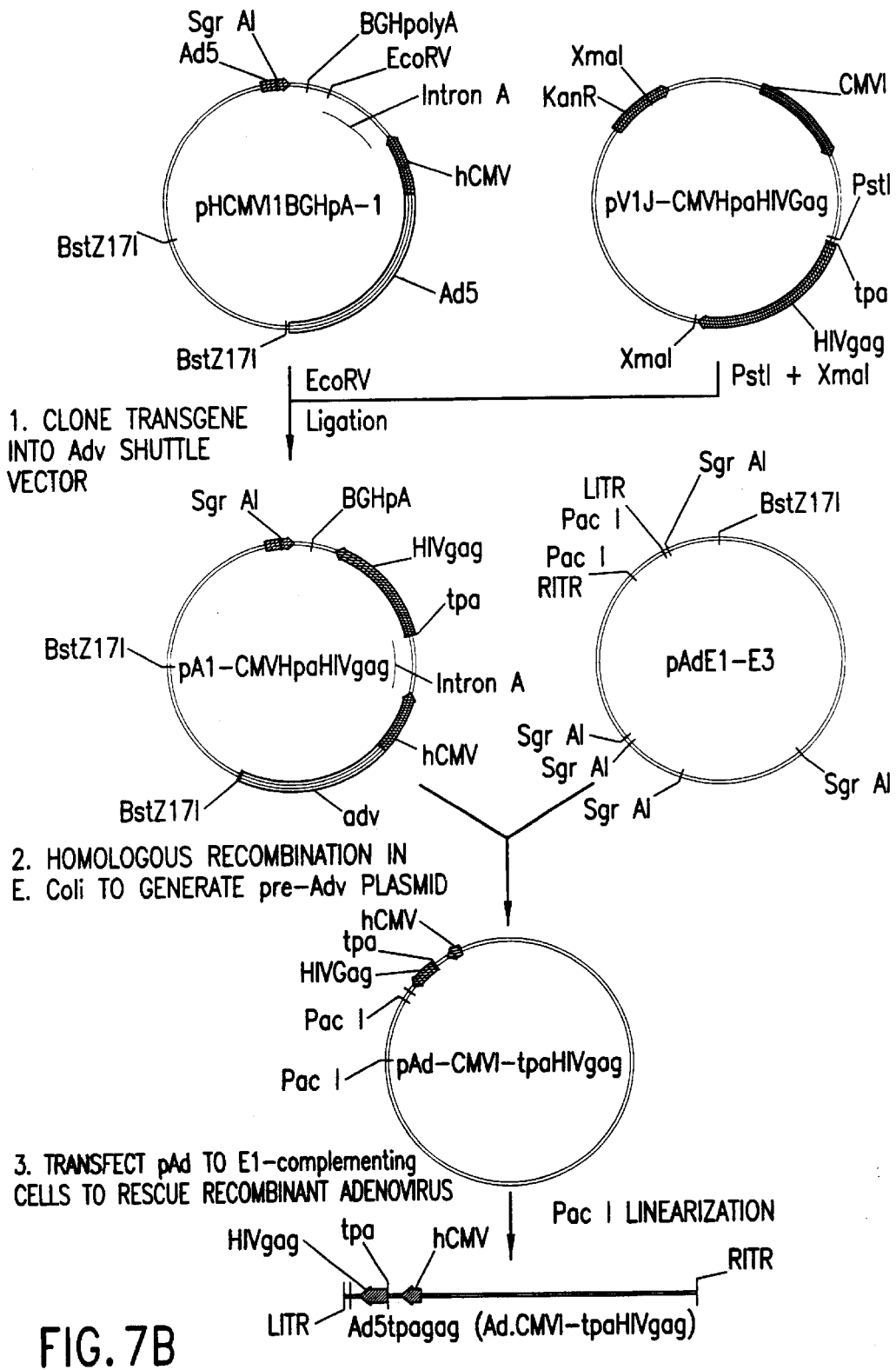
FIG. 7B shows construction of the adenovirus carrying codon-optimized tPA-gag.

FIG. 3 shows that all three monkeys had developed strong bulk culture cytotoxicity responses against gag peptide sensitized autologous B cell lines following in vitro restimulation using vaccinia-gag for two weeks. These responses were persistent at all time points tested although it is unclear whether the final inoculation at 24 weeks improved the cytotoxicities. In all cases killing is observed with at least one partial peptide pool (i.e. 25 peptides from amino terminus, 25 peptides from the carboxyterminus of gag). In every case killing is observed with the full peptide pool (all 50 peptides spanning the full-length gag). ELIspot assays showed high levels of gamma interferon secreting cells (approximately 200–1000 SFC/million PBMCs) over the course of these experiments, and CD4/8 depletion studies indicated that most responding cells were CD8 T lymphocytes, although most vaccines also had significant CD4 T cell responses.

Immunization of rhesus monkeys with FG adenovirus-5 FLgag.

Using a protocol similar to that described above, monkeys were vaccinated with a FG adenovirus-5 construct encoding a full-length gag gene (without the tPA leader peptide). This experiment compared a dose titration of vaccine as well as needle vs. biojector (a needleless injector) delivery at most doses. A third feature of this experiment addresses the concerns raised above about the possible negative effects that prior adenovirus immunity may have on adenoviral vector mediated vaccine responses.

While approximately 150 rhesus sera have been tested for anti-adenovirus-5 neutralizing antibody responses, no significant titers have been detected.

Rhesus are a poor host for this viral strain, while about 40–60% of humans have significant neutralizing antibody responses (titers from 10–500). For this experiment, two groups of monkeys (6 and 7) were pre-exposed to FG adenovirus-SEAP vectors thrice and once, respectively, generating a range of neutralizing antibody responses in these monkeys that encompass the range observed in humans.

FIGS. 4A–I show bulk culture cytotoxicity responses of these vaccines at 8 weeks post a single immunization. All monkeys (groups 1–5, FIGS. 4A–E) that had not been previously exposed to adenovirus-5 showed significant gag-specific cytotoxic responses at all doses using either biojector or needle while 5/6 vaccines that had been preexposed to adenovirus showed cytotoxic responses (groups 6–7, FIGS. 4F–G). Control animals have remained consistently negative in these assays (e.g., group 8, FIG. 4H).

Anti-gag ELIspot responses were also measured in all monkeys at eight weeks. Table 2, below is a summary of these responses that show that nearly all vaccines developed significant gamma-interferon responses to this vaccine, although prior exposure to adenovirus reduced response levels, and a dose response appears to have been obtained with the highest doses giving the best responses. In addition, in this experiment (as well as an independent experiment) no difference was observed for needle vs. biojector delivery of vaccine. CD4 T cell depletion of these samples showed that the ELIspot responses are largely due to CD8 T cells.

TABLE 2

Anti-gag ELIspot Responses of Rhesus Monkeys Immunized with FG adenovirus FLgag vaccine.

| Group | Rhesus # | Injection | Prior Adeno Exposure | SFC/million PBMCs media | gag pool H |
|---|---|---|---|---|---|
| 1 | 96R044 | Biojector | none | 6 | 663 |
| " | 96R045 | " | " | 0 | 665 |
| " | 96R046 | " | " | 5 | 893 |
| 2 | 96R047 | Biojector | none | 1 | 20 |
| " | 96R048 | " | " | 1 | 104 |
| " | 96R049 | " | " | 0 | 38 |
| 3 | 96R050 | Biojector | none | 4 | 18 |
| " | 96R051 | " | " | 1 | 14 |
| " | 96R052 | " | " | 10 | 48 |
| 4 | 96R053 | Needle | none | 1 | 410 |
| " | 96R054 | " | " | 0 | 125 |
| " | 96R057 | " | " | 3 | 186 |
| 5 | 96R058 | Needle | none | 1 | 93 |
| " | 96R060 | " | " | 1 | 41 |
| " | 96R062 | " | " | 0 | 6 |
| 6 | 940125 | Biojector | 3X $10^{10}$ FG aden-5 | 15 | 65 |
| " | 940132 | " | " | 11 | 39 |
| " | 940149 | " | " | 29 | 93 |
| 7 | 940145 | Biojector | 1X $10^{10}$ FG adeno-5 | 4 | 258 |
| " | 940147 | " | " | 15 | 578 |
| " | 940217 | " | " | 23 | 55 |
| 8 | 96R063 | none | none | 0 | 0 |
| " | 96R004 | " | " | 0 | 1 |

These and other data show that higher doses of FG adenovirus vaccines elicited ELIspot responses as high as 800–1000 SFC/million PBMCs (see Table 2). These responses are approximate 5–10 fold higher than those obtained using the highest doses of DNA gag vaccines after four injections over a six month time frame (see Table 3 below) indicating that FG adenovirus vaccines are much more potent than DNA vaccines. Importantly, these data also support the finding that repeated injection of adenoviral vector remain effective although somewhat attenuated in the presence of host immune response to adenovirus.

Combined DNA and FG Adenovirus Vaccinations in Rhesus.

DNA priming may enhance the cellular immune response to gag induced by adenovirus vaccination as shown below. Three rhesus monkeys which had been vaccinated four times with 1 mg of gag plasmid were boosted 4 months following the final DNA shot with 101 I particles of FG Ad FLgag. The cellular immune responses (measured by ELIspot and denoted as SFC/million PBMCs) to gag peptides in the monkeys primed with DNA and boosted with adenovirus appear significantly higher than adenovirus vaccination alone. The use of a DNA priming regimen may be particularly advantageous in humans who have preexisting anti-adenovirus immune responses.

TABLE 3

ELIspot Responses in Rhesus Monkeys After Combined DNA and FG adenovirus gag Vaccinations.

| | Monkey # | Priming | Vaccine | Week 20 (2 injections) | Week 28 (3 injections) |
|---|---|---|---|---|---|
| DNA prime/ Ad boost | 92x004 | DNA | Ad5tPAgag | 106 | 781 |
| | 93x027 | DNA | Ad5tPAgag | 88 | 660 |
| | 93x023 | DNA | Ad5tPAgag | 560 | 609 |
| DNA prime/ DNA boost | 93x008 | DNA | DNA | 344 | 285 |
| | 93x012 | DNA | DNA | NA | NA |
| | 93x016 | DNA | DNA | 106 | 99 |
| Naive/Ad | 92x024 | None | Ad5tPAgag | 373 | 898 |
| | 92x012 | None | Ad5tPAgag | 276 | 413 |
| | 94x025 | None | Ad5tPAgag | 531 | 1275 |
| Control | 088R | None | None | 5 | 84 |
| | 115Q | None | None | 0 | 8 |

Boost were performed at week 0, 8, and 24.

TABLE 4

Anti-gag antibody titer (mMU/ml) in Rhesus Monkeys After DNA and FG adenovirus gag Vaccinations.

| | Monkey # | Week 0 | Week 8 (1 injection) | Week 20 (2 injections) | Week 28 (3 injections) | Week 40 |
|---|---|---|---|---|---|---|
| DNA prime/ Ad boost | 92x004 | 25 | 7616 | 10133 | 12170 | 15892 |
| | 93x027 | 114 | 36666 | 20523 | 95114 | 31437 |
| | 93x023 | 41 | 11804 | 12485 | 38579 | 17422 |
| DNA prime/ DNA boost | 93x008 | 158 | 1689 | 817 | 3882 | 1626 |
| | 93x012 | <10 | 512 | 216 | 722 | 132 |
| | 93x016 | 20 | 305 | 451 | 2731 | 735 |
| Naive/ Ad | 92x024 | <10 | 2454 | 11460 | 15711 | 7449 |
| | 92x012 | <10 | 2161 | 5154 | 27029 | 8856 |
| | 94x025 | 14 | 5852 | 19159 | 45990 | 37586 |

Boost were performed at week 0, 8, and 24.

C. Determination of HIV-Specific T Lymphocyte Responses in HIV+Humans

In order to qualify the CTL assays, PBMCs from HIV-1-infected patients, classified as long-term nonprogessors (LTNPs) due to their ability to maintain low levels of systemic viremia and high $CD4^+$ T cell counts over a period of years, were used to measure systemic specific CTL responses. As discussed above, several studies have reported that the presence of HIV-1-specific CTL responses in infected individuals appears to correlate well with maintenance of disease-free infection.

Over the course of numerous independent experiments using PBMCs obtained from approximately 40 LTNPs at five different clinical centers, these HIV-infected individuals generally exhibited strong gag-specific ELIspot and cytotoxicity responses that are predominantly mediated by CD8+ T lymphocytes (CD4+ responses are typically extremely low or undetectable in HIV+ individuals). The overall gag-specific ELIspot responses determined in these experiments are summarized below:

HIV+ELIspot Response Summary
mean (±SD) SFC/million PBMCs (+gag peptides)= 980±1584
mean (+SD) SFC/million PBMCs (media control)=24±21

Similar experiments using PBMCs from 16 HIV seronegative individuals did not show significant gag-specific ELIspot or cytotoxicity responses. These ELIspot responses are summarized below:

HIV Seronegative ELIspot Response Summary
mean (±SD) SFC/million PBMCs (+gag peptides)=19±28
mean (±SD) SFC/million PBMCs (media control)=10±14

The ELIspot assay provides a quantitative determination of HIV-specific T lymphocyte responses by visualization of gamma interferon-secreting cells in tissue culture microtiter plates one day following addition of an HIV-1 gag peptide pool that encompasses the entire 500 amino acid open reading frame of gag (50 overlapping 20mer peptides) to PBMC samples. Gamma interferon was selected as the cytokine visualized in this assay (using species specific anti-gamma interferon monoclonal antibodies) because it is the most common, and one of the most abundant cytokines synthesized and secreted by activated T lymphocytes. For this assay, the number of spot forming cells (SPC) per million PBMCs is determined for samples in the presence and absence (media control) of peptide antigens. This assay may be set up to determine overall T lymphocyte responses (both CD8+ and CD4+) or for specific cell populations by prior depletion of either CD8+ or CD4+ T cells. In addition, ELIspot assays, or variations of it, can be used to determine which peptide epitopes are recognized by particular individuals.

A distinguishing effector function of T lymphocytes is the ability of subsets of this cell population to directly lyse cells exhibiting appropriate MHC-associated antigenic peptides. This cytotoxic activity is most often associated with CD8+ T lymphocytes but may also be exhibited by CD4+ T lymphocytes. We have optimized bulk culture CTL assays in which PBMC samples are infected with recombinant vaccinia viruses expressing antigens (e.g., gag) in vitro for approximately 14 days to provide antigen restimulation and expansion of memory T cells that are then tested for cytoxicity against autologous B cell lines treated either with peptide antigen pools. Specific cytotoxicity is measured compared to irrelevant antigen or excipient-treated B cell lines. The phenotype of responding T lymphocytes is determined by appropriate depletion of either CD8+ or CD4+ populations prior to the cytotoxicity assay. This assay is the best means for determining whether CTL responses were elicited by the vaccine.

Example 3

Clinical Trials

The safety and efficacy of a first generation adenovirus type 5 carrying an optimized gag gene alone and as part of a prime/boost protocol with a gag DNA plasmid are tested.

In the initial trial, subjects receive either 1 mg or 5 mg HIV gag DNA on a 0, 1, 2 month schedule. Equal number so of Ad5 seropositive and seronegative subjects are involved in the study.

In a second trial, Ad5 seropositive and seronegative individuals receive either $10^7$ or $10^9$ particles per dose on a 0, 6 month schedule. Some of the individuals who have received a single dose of $10^9$ particled of Ad5gag will also receive three injections of HIV gag DNA with $10^{11}$ particles of Ad5 gag. Also, individuals who are AdS seropositive and seronegative naïve individuals will receive $10^{11}$ particles on a 0, 6 month schedule.

Safety and immunogenicity parameters: Each individual is bled for serum prior to day 0 to determine AdS neutralization titers and for PBMCs to establish B-LCL lines for bulk CTL determinations. On day 0 and 4 weeks following each dose of Ad5 gag, PBMCs will be drawn to determine CTL using bulk CTL and ELIspot assays. Immunogenicity will also be measured at later time points to assess persistence of response.

Clinical Study Design Summary

1. Phase I study of HIV gag DNA Priming (plasmid only)

| GROUP | Vaccine (n) | Placebo (n) | DNA dose | DNA regimen | Ad5 Sero-status |
|---|---|---|---|---|---|
| 1 | 18 | 3 | 1 mg | 0, 1, 2 | + |
| 2 | 18 | 3 | 1 mg | 0, 1, 2 | − |
| 3 | 18 | 3 | 5 mg | 0, 1, 2 | + |
| 4 | 18 | 3 | 5 mg | 0, 1, 2 | = |
| TOTAL | 72 | 12 | | | |

2. Dose ranging study of AD5 gag

| GROUP | Vaccine (n) | Placebo (n) | Ad5 dose | Ad5 sero status |
|---|---|---|---|---|
| 1 | 8 | 2 | $10^7$ | + |
| 2 | 8 | 2 | $10^7$ | − |
| 3 | 8 | 2 | $10^9$ | + |
| 4 | 8 | 2 | $10^9$ | − |
| 5 | 15 | 2 | $10^{11}$ | + |
| 6 | 15 | 2 | $10^{11}$ | − |
| TOTAL | 62 | 12 | | |

3. Boosting of gag DNA by AdS gag

| Group | Vaccine | Placebo | Ad5 dose | Ad5 sero-status | DNA dose | DNA regimen |
|---|---|---|---|---|---|---|
| 1* | 15 | 2 | $10^{11}$ | + | 1 mg | 0, 1, 2 |
| 2* | 15 | 2 | $10^{11}$ | − | 1 mg | 0, 1, 2 |
| 3* | 15 | 2 | $10^{11}$ | + | 5 mg | 0, 1, 2 |
| 4* | 15 | 2 | $10^{11}$ | − | 5 mg | 0, 1, 2 |
| | 60 | 8 | | | | |

*represent the same subjects from Phase 1 study, above.

Example 4

Longevity of CMI Responses in Monkeys Vaccinated with Ad5-Flgag 69 weeks post the last vaccination (two injections at week 0 and 24), PBMC isolated from these monkeys were tested in unfractionated or CD4 T cell-depleted ELISPOT assays. The results in FIG. 9 show that high level of CMI responses were maintained in these vaccinees, and the responses were predominantly CD8+ as those detected following the $2^{nd}$ injection.

Example 5

Prime/Boost Regimens Utilizing V1JnsFLgag and/ or Ad5FLgag in Rhesus Monkeys

Rhesus monkeys immunized with HW gag DNA vaccine formulated with AlPO4 or the POP-POE copolymer CRL1005 (CytRx; Atlanta, Ga.) at 7.5 mg (injected at weeks 0, 4 and 8) were boosted with low dose adenovirus ($10^7$ particles) at week 24. The strategy of using the low dose adenovirus was adopted to mimic the prevalence of anti-adeno neutralizing Abs in vaccinees, based on our early observation that the presence of anti-adeno Ab titers in rhesus monkeys will effectively reduce the vaccination dose by two to three orders of magnitudes. It has also been shown that this dose of Ad5-FLgag is not efficient in priming CMI responses in monkeys, judged by the respective ELISPOT responses. The prime-boost results showed, however, that this low dose of Ad5 vaccines is highly efficient in boosting immune responses primed with DNA vaccines. The prime-boost strategy outlined here provides an alternative vaccination regimen to overcome the anti-Ad5 seroprevalence in human population. FIG. 10 shows CMI responses prior to and subsequent to the week 24 boost with Ad5-Flgag. These data show that adjuvant formulations of DNA primed CMI responses more efficiently than naked DNA in saline.

FIG. 11 shows long term CMI responses for an HIV gag DNA vaccine (0, 4 and 8 weeks) and Ad5FLgag (single prime at T=0) which were boosted with $10^7$ particles of Ad5FLgag.

Figure 12:
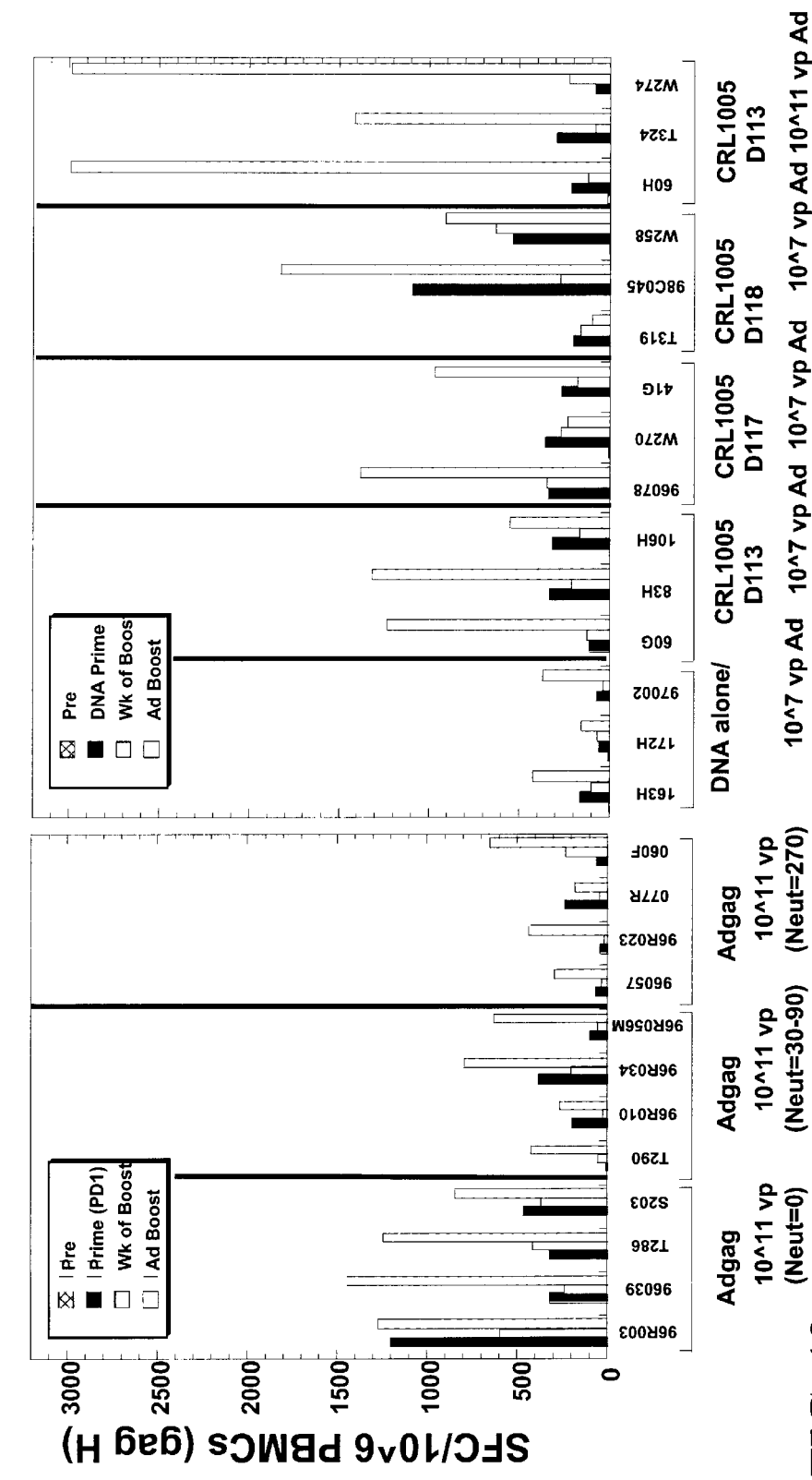
FIG. 12 shows a comparison of various single modality Ad5FLgag immunizations with DNA gag vaccines adjuvanted with various formulations of CRL1005. (D113:5 mg/ml DNA, 7.5 mg CRL1005 in PBS; D117:5 mg/ml DNA, 22.5 mg CRL1005 in PBS; D118:7.5 mg/ML CRL1005, 0.5 mM BAK and 5 mg/ml, DNA in PBS. DNA/POP-POE/BAK formulations are disclosed in U.S. Provisional Application Ser. Nos. 60/214,824 and 60/213622, filed Jun. 28, 2000 and Jun. 23, 2000, respectively; both of which are hereby incorporated by reference.) Four columns of data are presented for each animal. The far left column is a pre-immunization ELISPOT response; the column second from the left represents the ELISPOT after either the AdS or DNA priming, respectively; the column third from the left is taken the week of or prior to the boosting, and the fourth column measures a CMI response subsequent to the Ad5FLgag boost.
Figures 14A, 14B, 14C:
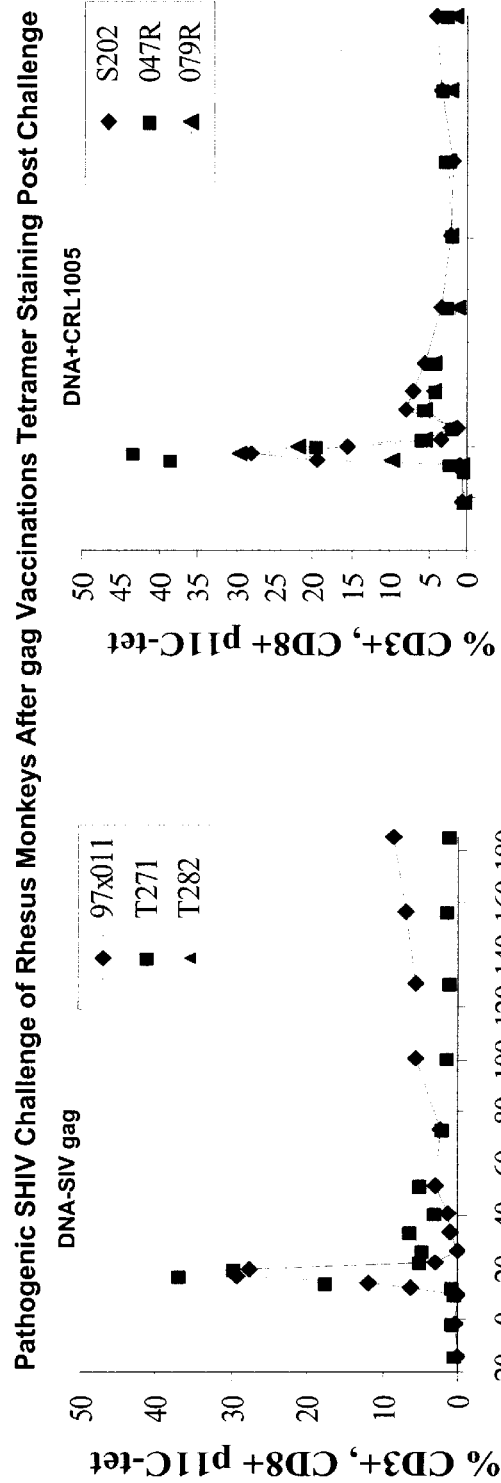
Figure 15B:
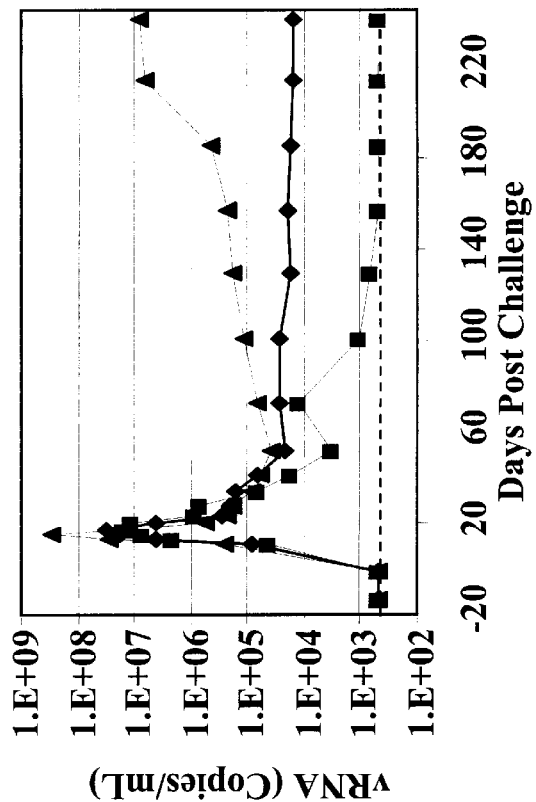
Figure 15A:
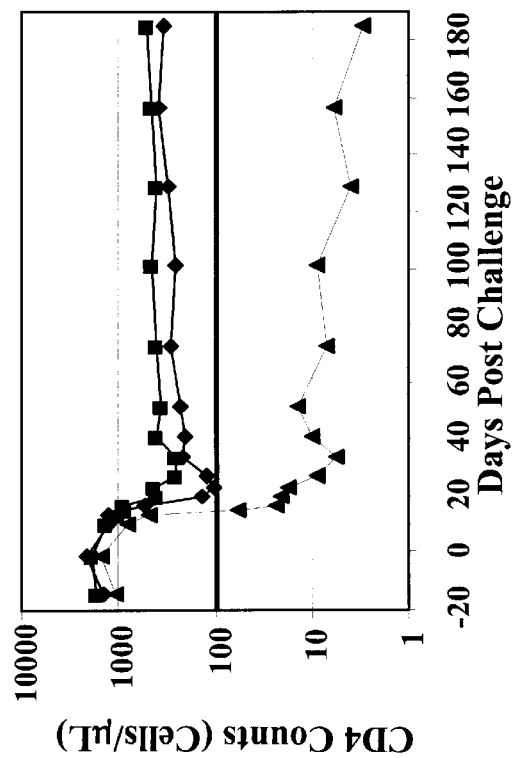
Figures 15K, 15L:
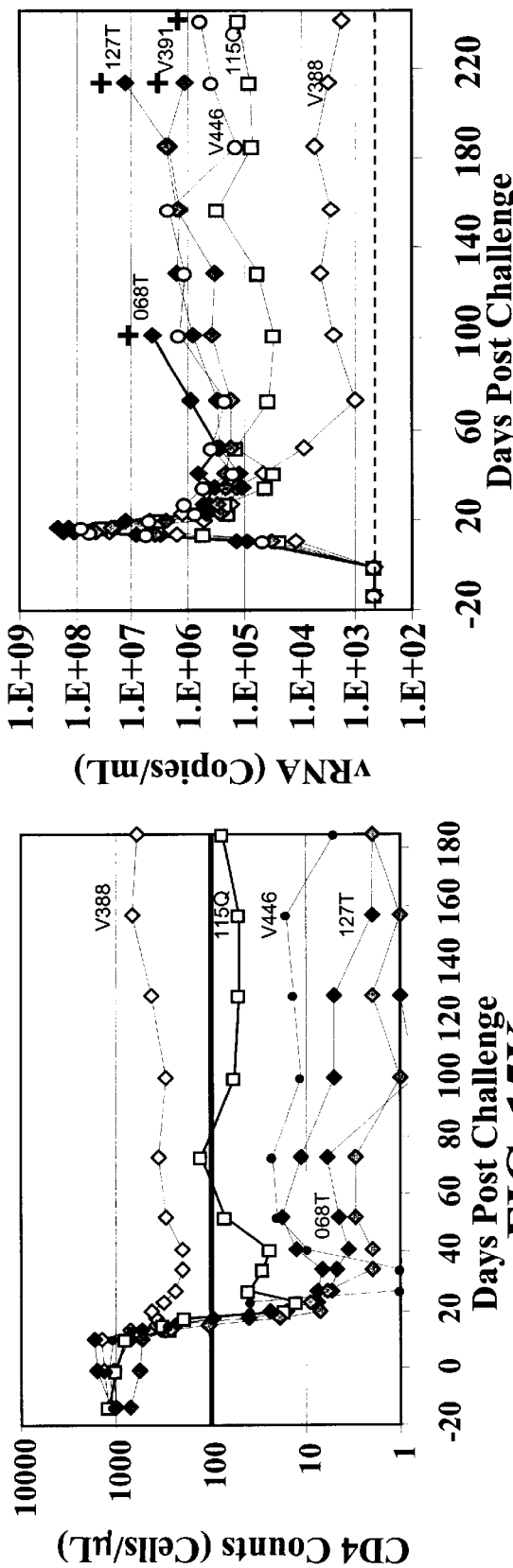

FIG. 12 shows data that compares the cellular immune response for various prime/boost regimens. Three groups shown in the left three panels received adenoviral vector prime and adenoviral vector boost at $10^{11}$ particle dose (week 0 and 24). The five DNA-primed (week 0, 4, 8) groups shown in the right five panels received adenoviral vector at either $10^7$ or $10^{11}$ particles (week 24). Different CRL-1005 formulations were tested for their ability to enhance the immunogenicity of DNA vaccination (D113, D117 and D118: D113 is 5 mg/ml DNA, 7.5 mg CRL1005 in PBS; D117 is 5 mg/ml DNA, 22.5 mg CRL1005 in PBS; and D118 is 7.5 mg/mL CRL1005, 0.5 mM BAK and 5 mg/mL DNA in PBS. DNA/POP-POE/BAK formulations are disclosed in U.S. Provisional Application Ser. Nos. 60/214,824 and 60/213622, filed Jun. 28, 2000 and Jun. 23, 2000, respectively; both of which are hereby incorporated by reference). The data showed: 1) pre-existing anti-adeno titers in vaccinees reduce the priming and boosting efficacy of the Adenoviral vector expression HIV-1 gag; 2) DNA priming can overcome the low dose adenoviral vector boost; 3) efficiency of priming with DNA vaccine can be improved with adjuvanting of CRL-1005; and 4) CRL-1005 DNA priming coupled with low dose adenoviral vector boosting can induce CMI responses equivalent to those seen in adenovirus-naïve monkeys received $10^{11}$ particles of the adenoviral vector expressing HIV-1 gag. Therefore, while there may be attenuation of the response to a defective adenovirus gag vector mediated by pre-existing neutralizing antibodies, a portion of the present invention, in view of this data, relates to the ability to overcome any such attenuation by a prime/boost immunization regime with a priming by a selected DNA plasmid formulation expressing the HIV-1 Gag antigen, followed by a boosting with an adenovirus vector expressing the Gag antigen.

Example 6

Evaluation of SIVmac239 Gag-Based Vaccines for Protection of Rhesus Macaques Against Challenge of SHIV89.6P Materials and Methods—Animals Fifteen rhesus monkeys (*Macaca mulatta*) were assigned in five groups received vaccines, while 6 were assigned as naïve control monkeys that did not receive any vaccination. All monkeys were typed for Mamu-A*01 allele expression according to PCR-SSP methodology. Briefly, genomic DNA was extracted from monkey PBMC or B lymphoid cells using QiaAmp DNA Kit (Qiagen), and about 20 ug to 100 ng of DNA was used for PCR reactions. Two pairs of primers were used, one for detection of a fragment within Mamu-A*01 allele, and one for a fragment within Mamu-DRB region to serve as positive control for PCR reaction. All animals that tested positive in PCR reaction were confirmed by sequencing methods.

Vaccines and Vaccination Regimen

Codon optimized SIVmac239 p55 gag gene (no pol sequences) was constructed with annealing of a series of overlapping oligonucleotides. The authenticity of the synthetic gene was confirmed with DNA sequencing. The gene was cloned into V1Jns, as disclosed herein. The same synthetic gene was cloned into either MVA or adenovirus vectors. Regarding recombinant MVA vector construction, the codon optimized SIV gag gene with an authentic Kozak sequence (GCCACC) in front of ATG was PCR amplified and cloned into the pSC59 shuttle vector. The vector was designed to insert the transgene fragment into the viral thymidine kinase region, and to drive the transgene from a synthetic early/late promoter. The recombinant vector was selected through plaque assay six times, and confirmed each time based on immunostaining method. The selected clones were expanded, purified, and transgene expression was confirmed by Western blot analysis. The adenovirus vector was generated by cloning the codon optimized SIV gag gene fragment downstream of the CMV promoter with noIntron A region into an adenoviral shuttle vector. All constructs were confirmed for expression by Western blot analysis. The plasmid DNA vaccine expressed the codon optimized SIV gag gene utilizing a CMV promoter in a V1Jns plasmid vector backbone. Therefore, the vaccine groups were as follows:

(1) Naïve Controls (MamuA1+ and MamuA1− monkeys);
(2) MVA SIV gag ($10^9$ pfu);
(3) Ad5 SIV gag ($10^{11}$ viral particles~$10^9$ pfu);
(4) SIV gag DNA (5 mg);
(5) SIV gag DNA (5 mg)+CRL-1005 (CytRx, Atlanta, Ga.)
(6) SIV gag DNA (5 mg)+Alum/MPL Plasmid DNAs were injected at weeks 0, 4, 8, 32. MVA and Adenovirus vectors were injected at weeks 0, 6, 32. The monkey were SHIV challenged (50 MID5o intravenously) at week 44, which was 12 weeks post last immunization. SHIV 89.6P is a HIV-1/SIV-1 chimera (HIV-1 tat, rev, env; with a SIV backbone). HIV env of SHIV 89.6P is derived from a primary, dual tropic viral isolate, which is rendered highly viremic and pathogenic by serial in vivo passage. SHIV 89.6 causes acute CD4 lymphopenia (typically in 7–21 days, while causing AIDS and death in 1–2 years.

Tetramer Staining

The method for preparing p11C tetramer reagent and staining whole blood is as follows: PE-labeled tetrameric Mamu-A*01/peptide complexes was used in conjunction with PerCP-labeled anti-human CD8$^+$(SK1; Becton Dickinson), and APC-labeled anti-rhesus monkey CD3 (FN18) monoclonal antibodies to stain peptide-specific CD8$^+$T cells. A sample of 100 μl whole blood from the vaccinated monkeys was directly stained with these reagents, lysed, washed, and fixed. Samples were analyzed through flow cytometry on FACScalibur [Becton Dickinson (BD), San Jose, Calif.], and gated CD3+CD8+T cells were examined for staining with tetrameric Mamu-A*01/p11 C, Mamu-A*01/p41 A, or Mamu-A*01/p68A complexes. For each sample, 30,000 gated CD3+/CD8+ lymphocyte events were collected and analyzed on CellQuest program (BD).

ELSIPOT Assay

Sterile 96-well microtiter plates with well bottoms of polyvinylidene difluoride (PVDF, MAIP S45, Millipore) were coated overnight at 4° C. with 100 µl/well of mouse anti-human IFN-γ monoclonal antibody (R&D Systems). The antibody was diluted to 10 µg/ml in sterile PBS. Coated plates were washed four times with sterile PBS and blocked 2 hours at 37° C. with 200 µl/well of R10 complete medium (RPMI-1640 plus 10% heat-inactivated fetal bovine serum plus supplements). Blocking buffer was decanted and 100 µl/well of rhesus PBMC diluted in R10 were added to result in $2 \times 10^5$ and $1 \times 10^5$ cells/well. Synthetic peptide antigens were added to the PBMC wells in duplicate at a final concentration of 2.5 µg/ml per peptide. Peptide-free DMSO diluent matching the DMSO concentration in the peptide solutions was used as a negative control (medium control). The peptide pools were composed of 20-mer peptides overlapping by 10 amino acids, representing N-terminal or C-terminal half of SIV gag (SIVmac239) and env (89.6P, KB9 clone) gp120 regions. The peptides containing p11C epitope was deleted from the SIV gag peptide pool for the purpose of detecting other epitopes besides p11C. Plates were incubated 24 hours in a humidified $CO_2$ incubator at 37° C. and then washed 7 times with PBS containing 0.05% Tween 20 (Sigma). Biotinylated goat anti-human IFN-γ monoclonal antibody (R&D Systems catalog #BAF285) was diluted to 0.1 µg/ml in assay diluent consisting of PBS and 5% heat inactivated fetal bovine serum (FBS, HyClone) and 0.005% Tween 20. Diluted antibody was added to the plates at 100 µl/well and incubated overnight at 4° C. After washed 7 times with PBS/Tween, 100 µl/well of alkaline phosphatase-conjugated streptavidin (B-D PharMingen, San Diego, Calif.) at 1:2500 in assay diluent was added to each well. Plates were incubated 2 hours at room temperature and washed 7 times with PBS/Tween. To develop the spots, 100 µl/well of precipitating alkaline phosphatase substrate NBT/BCIP (Pierce) was added to each well and incubated at room temperature until spots became visible, usually 5–10 minutes. Substrate was decanted and plates rinsed three times with deionized water. After plates had air-dried overnight, spots were counted with a stereomicroscope using a magnification of 20–25×. The number of spots per well at each cell input was normalized per $1 \times 10^6$ cells and averaged for each sample and antigen.

Cytotoxicity Assay

The methods describing generation of B lymphoblastoid cell lines and bulk culture cytotoxicity assay have described previous (JV. Accepted). Instead of using vaccinia virus for restimulation, recombinant Ad5SIV gag was used for CTL cultures from MVA-SIVgag-vaccinated animals.

Results

Improved expression is shown by utilizing a SIV gag gene codon optimized for expression in mammalian systems. The SIVmac 239 gag open reading frame was optimized in this fashion for expression. There were about 60% nucleotide changes in the synthetic gene, corresponding to about 20% of codons. The improvement in expression of the optimized gene in comparison of wild type SIV mac 239 gag was confirmed in Western blot analysis.

The other vaccine modalities used in this study include two viral vectors, adenovirus vector which has both E1 and E3 regions deleted, and an MVA vector which has the transgene inserted at the TK region. The transgene in MVA vector is driven by a synthetic early/late promoter. The transgene in the adenoviral vector is driven by CMVie promoter and enhancer without intron A region.

Twenty one monkeys were assigned in this study, allocated into one naïve control group of six monkeys, and five vaccination groups with 3 monkeys per group. All monkeys were typed for Mamu-A*01 allele, and all monkeys in the vaccination groups except one monkey in the DNA group were Mamu-A*01 monkeys. The expression of this MHC allele facilitated the analysis of CD8 T cell immune response to vaccination with a tetramer reagent directed against a prevalent SIV gag epitope, p11C. To insure the appropriate priming, all viral vaccine vectors were administrated twice at week 0 and 6, and all DNA vaccines three times at week 0, 4, and 8. After a long rest of at least three months, all monkeys were boosted with the same dose of priming modality.

Pre-Challenge Immunogenicity Study

FIGS. 13A–E shows the longitudinal p11C-specific tetramer staining results for all Mamu-A*01 monkeys up to one week before challenge. All results are expressed as % CD3+CD8+positive T cell population. Following two priming injections, all three monkeys in the MVA group showed significant tet positive staining with the highest one reaching 1.6%, and the average close to 0.7%. The response in this group gradually declined, and was close to detection limit right before the boost (0.1%). However, the boost injection with the same dose MVA did not improve the overall percentage of tet positive staining, and the peak of responses at two weeks post boost injection in all three monkeys is lower than their initial height of staining following priming injections. Before challenge at week 44, all three monkeys are stained positive just above 0.1%. The tetramer staining in the adenovirus-immunized group showed much higher staining, with the average of the staining at over 2% following two priming injections. The responses reached stead level of about 0.3 to 1.2% before the boost, and were significantly boosted with staining at 3 to 5.5% in all three monkeys. The staining was stead at 1–2% before challenge. All DNA vaccine groups received three priming injections, and all monkeys demonstrated detectable tetramer staining except the Mamu-A*01 negative monkey T282. The most noticeable group is the CRL1005 adjuvanted group, with a monkey reaching 2% tet staining following priming injections (S202). The results from MPL/alum group are similar to those of the DNA/saline group. Following boost injection, all vaccinees are significantly boosted, with average staining in each group 2–3-fold higher than their respective peak staining following priming injections. At week 37 (one week before challenge), the DNA/CRL1005 group maintained about 0.3 to 0.7% tetramer positive staining, whereas both DNA in saline and MPL/alum groups were at about 0.1 to 02%.

ELISPOT assay was performed with unfractionated PBMC samples collected two weeks after series of priming injections. The results showed that all Mamu-A*01 vaccinees have developed IFN-g ELISPOT response against p 1 IC peptide. These responses in general correlate with their tetramer staining, with adenovirus group showing the highest average spot counts, followed by the CRL-1005 group, MPL/alum group, and DNA in saline group. The MVA inoculation induced high background spot counts in all three rhesus monkeys, thus the results could not be interpreted meaningfully. It is noted that many vaccinees also developed T cell responses against T cell determinants other than p11C epitope, as both N- and C-terminal peptide pools contained no p11C epitope sequence. This is especially noticeable for the adenovirus-immunized group, as all three monkeys have developed responses against extra-p11C responses.

Challenge Data and Disease Progression

Twelve weeks post the boost, all monkeys were challenged with 50 MID50 of SHIV 89.6P intravenously. All monkeys were infected, demonstrated acute viremia within 3 weeks post infection that is typical of this viral stock (see FIGS. 14A–F). Post challenge longitudinal results for peripheral p11C-specific tetramer staining are presented for each group (FIGS. 14A–F), as well as CD4 T cell counts and plasma viral load for each group (FIGS. 15A–L). The six monkeys in the naïve control group demonstrated the rapid CD4 T cell lymphopenia within 3 weeks after challenge. The peak viral loads reached 10A8 copies/ml that is typical for SHIV 89.6P. There is very low tetramer staining cells in the two Mamu-A*01 monkeys in this group. One exception in this group is a Mamu-A*01 monkey, V388, who maintained CD4 counts over 300 cell/ul. Its viral load gradually declined after peaked around day 14 to 17 coincide with an about 2% tetramer staining for p11C epitope. Low but consistent level p11C tetramer staining is detectable during the course of follow-up, maintained at about 0.8–1.0%. No monkeys in MVA-vaccinated group were protected against CD4 loss, although 15G maintained CD4 T cell counts above 300 cells/ml through the acute phase. The peak viremia for the group was indistinguishable for that of naïve control group, but their VL at the chronic stage were significantly lower than those of control group. At the day 180 post challenge, two out three monkeys maintained viral load around 1000 copies/mL, while the third on 10000 copies/mL. All three vaccinees in the adenovirus group achieved protection against CD4 loss upon viral challenge, as all of them maintained CD4 counts well above 500 cells/ml though the course of the study. It is also noticeable that peak viral loads in all three monkeys were at least one log lower than those in control naïve monkeys, and viral loads in all three monkeys become undetectable after day 180 post challenge (under 500 copies/mL). The nine vaccinees in three DNA vaccinated groups were not protected against acute CD4 lymphopenia post viral challenge, except one monkey in MPL/alum group (058R). This monkey maintained CD4 counts over 500 cells/µL through acute phase. The peak viral loads of these groups were not significantly different from that of naïve control monkeys. However, the viral loads on day 180 post challenge of all three groups were lower than those of naïve control monkeys (1–2 log reduction). The most noticeable is the DNA/CRL1005 group, where their viral loads of two out of three monkeys were below the detection limit (500 copies/mL). Immunodeficiency related diseases were reported for five of the six naïve control monkeys, and four have died or been sacrificed by day 240 post challenge per attending veterinarians' recommendation. No vaccinees have developed any immunodeficiency syndromes or suffered any consistent weight loss.

Post-Challenge Immune Response Analysis

To define the T cell responses in control of viral replication post challenge, unfractionated PBMC were tested in IFN-γ ELISPOT assay against p11C peptide, the SIV gag peptide pool (N-plus C-ter peptide pool), and 89.6P env gp120 peptide pool. Strong ELISPOT responses against SIV gag antigen (peptide pool or p11C peptide) were observed in all vaccinees, but none in the naïve control monkeys. The average of spots for each vaccination group correlates with their p11C tetramer staining. No significant responses were observed for env 89.6 antigen peptide pool, and in general they were lower than their respective anti-p11C or anti-SIV gag responses. These results support the immune dominance status of p11C epitope as indicated by longitudinal tetramer staining results. To differentiate the subset of T cells accounting for IFN-γ production, IFN-γ intracellular staining along with T cell surface marker staining (CD3, CD4, CD8) was performed on PBMC cells that were stimulated with these peptide pools All vaccinees in adenovirus group exhibited CD4 response against SIV gag, in contrast to naïve control monkeys. No meaningful CD4 responses could be registered in the CRL1005 group and the MVA group because of severe CD4 T cell lymphopenia. All monkeys in adenovirus group exhibited CD8 T cell responses against SIV gag peptide pool missing p11C peptide, indicating that additional T cell determinants were recognized. This is also the case for one monkey in MPL/alum group, 058R.

Serum samples from these monkeys were tested for their neutralizing titers against SHIV89.6P virus. Neutralizing Abs appeared mostly during week 3–4 post challenge, with some achieved as early as week 2 post challenge (97×011 and 058R). However, no specific correlation with the virological parameters could be identified, as the monkeys in Ad5-SIV gag and DNA/CRL1005 groups controlled their viral load at the chronic stage with the late appearance of neutralizing Ab titers. These results indicated that cellular immune response induced by SIV gag-based vaccines, not a humoral Ab response, was protective in this experiment against challenge of SHIV89.6P. The correlation coefficiency analysis was performed on pre challenge tetramer staining result (CMI response induced by SIV gag vaccination) and plasma viral load at day 180 post challenge. The negative correlation was revealed with $R=-0.685$ and $p<0.003$.

Histological analysis was performed on lymph nodes collected around day 120 post challenge on selected monkeys. While SHIV RNA could readily be detected in the lymph nodes from naïve control monkeys by in situ hybridization, very few infected T cells could be found in the slides derived from LN samples of monkeys in ad5-SIVgag and DNA-CRL1005 groups. Quantitation of these SHIV RNA+ cells indicated that there were greater than 10 fold reduction in number of virus-infected cells in LN for both Ad5-SIV Gag and DNA/CRL1005 groups. Staining CD4 T cells showed that Ad5-SIV gag vaccinated monkeys preserved the CD4 T cells, while both naïve control and DNA/OptiVax groups suffered severe CD4 T cell depletion.

This example evaluates the role of CD8+cytotoxic T lymphocytes (CTL) in controlling SIV infection in rhesus macaques. To directly compare the efficacy of various vaccine vectors for induction of protective CMI responses, monkeys were immunized with three vaccines expressing SIVmac239 gag:(1) a MVA vector; (2) an adenovirus vector, and (3) a plasmid DNA vector. The DNA vaccine was formulated either in saline, with adjuvants including synthetic polymers (CRL1005, from CytRx), and monophospholipid A absorbed on alum (MPL/Alum). The immunogenicity of these vaccines was compared directly in rhesus monkeys using class I tetramer that was specific for a CTL epitope restricted with Mamu-A*01 allele. Cellular immune responses were also evaluated with peptide pools covering SIV gag region using ELISPOT assay. Three months post the last vaccination, all monkeys were challenged intravenously with pathogenic Simian-human Immunodeficiency virus (SHIV), SHIV-89.6P. As shown herein, five out of six naïve control monkeys showed rapid loss of $CD4^+T$ cells, higher setpoint viral loads, and four succumbed to immunodeficiency syndromes and sacrificed within six months post challenge. All the vaccinees were infected but demonstrated potent amnestic CTL responses judged by SIV gag CTL epitope tetramer staining. All monkeys exhibited various degrees of protections correlated with their pre challenge tetramer staining. Adenoviral vector vaccinated monkeys were protected from acute CD4+ lymphopenia, and their plasma viral loads were below the detectable limit (<500 copies/mL) six months post challenge. The monkeys in the DNA/CRL1005 group were not protected from CD4+lymphopenia, but their viral load at 6 months post challenge were below 500 copies/mL. These results further support earlier examples disclosed herein: that vaccine-elicited CTL responses are capable of controlling a highly pathogenic AIDS virus challenge and preventing immunodeficiency, clinical disease progression, and death.

In conclusion, the Ad5 and DNA/CRL1005 immunized monkeys had lower levels of virus in their blood than did the control animals (~100 to 1000-fold lower). Five of 6 controls have exhibited AIDS-related illnesses since infection while 0 of 6 adenovirus and DNA/Optivax vaccinees have shown AIDS-related illnesses. Four out of 6 controls have died (euthanized at the discretion of attending veterinarians to prevent suffering) while 0 of 15 vaccinees (all groups taken together) have died. The Adenovirus SIV gag vaccine elicited more potent cellular immune responses than other vaccines evaluated and apparently protected more effectively from SHIV challenge. The degree of protection during chronic viremia appears to associate with relative immunogenicity prior to challenge, and with the development of multi-epitopic responses after challenge. Finally, these data demonstrate that vaccine-mediated cellular immunity directed only against gag, without priming for anti-env Abs, can provide significant control of SHIV infection in rhesus monkeys

What is claimed is:

1. A vaccine composition comprising a replication defective adenoviral vector comprising at least one gene encoding a HIV gag protein which is codon optimized for expression in a human, and the gene is operably linked to a heterologous promoter and transcription terminator.

2. An adenoviral vaccine vector comprising:
   a) a replication defective adenoviral vector, wherein the adenoviral vector does not have a functional E1 gene, and further comprising:
   b) a gene expression cassette comprising:
      i) a nucleic acid encoding a gag protein which is codon optimized for expression in a human host;
      ii) a heterologous promoter operatively linked to the nucleic acid encoding the gag protein; and
      iii) a transcription terminator.

3. A vector according to claim 2, wherein the E1 gene has been deleted from the adenoviral vector.

4. A vector according to claim 3, wherein the gene expression cassette has replaced the deleted E1 gene.

5. A vector according to claim 3, wherein the adenovirus vector does not have a functional E3 gene.

6. A vector according to claim 5 wherein the E3 gene has been deleted from the replication defective adenoviral vector.

7. A vector according to claim 6 comprising adenoviral 5 sequences deleted of E1 region base pairs (bp) 342–3523 and deleted of E3 region bp 28,133–30,818.

8. A vector according to claim 6 comprising adenoviral 2 sequences deleted of E1 region bp 559–3503 and E3 region bp 28,812–29,773.

9. A vector according to claim 8 comprising the sequence given in FIG. 6.

10. A vector according to claim 8 wherein the sequence is tPA-gag.

11. A vector according to claim 2 further comprising a physiologically acceptable carrier.

12. An adenoviral vaccine composition for producing an immune response against human immunodeficiency virus (HIV) in a human comprising:
   a) adenovirus serotype 5 sequences bp 1 to bp 341 and bp 3534 to 5798; and
   b) a gene expression cassette, located 3' to adenovirus sequence bp 341, comprising:
      i) a nucleic acid encoding gag which is codon-optimized and optionally has the tPA leader sequence at its 5' end;
      ii) a human CMV promoter plus intron A operatively linked to the nucleic acid encoding gag; and
      iii) a bovine growth hormone transcription terminator.

13. A plasmid vector comprising:
   a) an adenoviral portion comprising an adenoviral vector according to claim 2; and
   b) a plasmid portion.

14. A cell comprising an adenoviral vector of claim 2.

15. A method of producing the vector of claim 2 comprising introducing the adenoviral vector of claim 2 into a host cell which expresses adenoviral E1 protein, and harvesting the resultant adenoviral vectors.

16. A method according to claim 15 wherein the cell is a 293 cell or PER.C6 cell.

17. A method of generating a cellular immune response against an HIV protein in an individual comprising administering to the individual at least one adenovirus vaccine vector and a vaccine plasmid, wherein said adenovirus vaccine vector comprises:
   a) a replication defective adenoviral vector, wherein the adenoviral vector does not have a functional E1 gene, and
   b) a gene expression cassette comprising: i) a nucleic acid encoding gag protein optimized for expression in a human host; ii) a heterologous promoter operatively linked to the nucleic acid encoding the gag protein; and iii) a transcription terminator; and wherein said vaccine plasmid comprises:
   a) a gene expression cassette comprising: a nucleic acid encoding a gag protein, wherein the nucleic acid is codon optimized for expression in a human host;
   b) a promoter; and
   c) a transcription terminator
   wherein the vaccine plasmid does not contain any adenoviral genes.

18. A method according to claim 17 comprising administering a vaccine plasmid to the individual, and after a predetermined minimum amount of time has passed, administering an adenovirus vaccine vector to the individual.

19. A method according to claim 17 comprising administering an adenovirus vaccine vector to the individual, and after a predetermined minimum amount of time has passed, administering a vaccine plasmid to the individual.

20. A method according to claim 17 comprising administering an adenovirus vaccine vector to the individual, and after a predetermined minimum amount of time has passed, re-administering an adenovirus vector to the individual.

* * * * *

SEQUENCE LISTING

```
<160> NUMBER OF SEQ ID NOS: 4

<210> SEQ ID NO 1
<211> LENGTH: 1532
<212> TYPE: DNA
<213> ORGANISM: Artificial Sequence
<220> FEATURE:
<223> OTHER INFORMATION: Optimized human HIV-1 gag ORF

<400> SEQUENCE: 1
agatctacca tgggtgctag ggcttctgtg ctgtctggtg gtgagctgga caagtgggag      60
aagatcaggc tgaggcctgg tggcaagaag aagtacaagc taaagcacat tgtgtgggcc    120
tccagggagc tggagaggtt tgctgtgaac cctggcctgc tggagacctc tgagggggtgc   180 aggcagatcc tgggccagct ccagcccctcc ctgcaaacag gctctgagga gctgaggtcc   240
ctgtacaaca cagtggctac cctgtactgt gtgcaccaga agattgatgt gaaggacacc    300
aaggaggccc tggagaagat tgaggaggag cagaacaagt ccaagaagaa ggcccagcag    360
gctgctgctg gcacaggcaa ctccagccag gtgtcccaga actaccccat tgtgcagaac    420
ctccagggcc agatggtgca ccaggccatc tcccccccgga ccctgaatgc ctgggtgaag    480
gtggtggagg agaaggcctt ctcccctgag gtgatcccca tgttctctgc cctgtctgag    540
ggtgccaccc cccaggacct gaacaccatg ctgaacacag tgggggggcca tcaggctgcc    600 atgcagatgc tgaaggagac catcaatgag gaggctgctg agtgggacag gctgcatcct    660
gtgcacgctg gccccattgc ccccggccag atgagggagc ccaggggctc tgacattgct    720
ggcaccacct ccaccctcca ggagcagatt ggctggatga ccaacaaccc ccccatccct    780 gtggggggaaa tctacaagag gtggatcatc ctgggcctga acaagattgt gaggatgtac    840
tcccccacct ccatcctgga catcaggcag ggccccaagg agcccttcag ggactatgtg    900
gacaggttct acaagaccct gagggctgag caggcctccc aggaggtgaa gaactggatg    960
acagagaccc tgctggtgca gaatgccaac cctgactgca gaccatcct gaaggccctg    1020 ggccctgctg ccacccctgga ggagatgatg acagcctgcc aggggggtggg gggccctggt   1080 cacaaggcca gggtgctggc tgaggccatg tcccaggtga ccaactccgc caccatcatg    1140
atgcagaggg gcaacttcag gaaccagagg aagacagtga agtgcttcaa ctgtggcaag    1200
gtgggccaca ttgccaagaa ctgtagggcc cccaggaaga agggctgctg gaagtgtggc    1260
aaggagggcc accagatgaa ggactgcaat gagaggcagg ccaacttcct gggcaaaatc    1320
```

```
tggccctccc acaagggcag gcctggcaac ttcctccagt ccaggcctga gcccacagcc    1380
cctcccgagg agtccttcag gtttggggag gagaagacca cccccagcca gaagcaggag    1440
cccattgaca aggagctgta ccccctggcc tccctgaggt ccctgtttgg caacgacccc    1500
tcctcccagt aaaataaagc ccgggcagat ct                                  1532
```

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2

```
tagcggcgga gcttctacat c                                                21
```

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3

```
actgggagga ggggtcgttg c                                                21
```

<210> SEQ ID NO 4
<211> LENGTH: 1482
<212> TYPE: DNA
<213> ORGANISM: Artificial Sequence
<220> FEATURE:
<223> OTHER INFORMATION: Optimized tPA gag ORF

<400> SEQUENCE: 4

```
atggatgcaa tgaagagagg gctctgctgt gtgctgctgc tgtgtggagc agtcttcgtt      60
tcgcccagcg agatctccat tgtgtgggcc tccaggagc  tggagaggtt tgctgtgaac     120
cctggcctgc tggagacctc tgaggggtgc aggcagatcc tgggccagct ccagcccctcc    180 ctgcaaacag gctctgagga gctgaggtcc ctgtacaaca cagtggctac cctgtactgt     240
gtgcaccaga gattgatgt gaaggacacc aaggaggccc tggagaagat tgaggaggag      300
cagaacaagt ccaagaagaa ggcccagcag gctgctgctg gcacaggcaa ctccagccag    360
gtgtcccaga ctaccccat tgtgcagaac ctccagggcc agatggtgca ccaggccatc      420
tcccccggga ccctgaatgc ctgggtgaag gtggtggagg agaaggcctt ctcccctgag     480
gtgatcccca tgttctctgc cctgtctgag ggtgccaccc ccaggacct gaacaccatg      540 ctgaacacag tgggggggcca tcaggctgcc atgcagatgc tgaaggagac catcaatgag    600
gaggctgctg agtgggacag gctgcatcct gtgcacgctg gccccattgc ccccggccag    660
atgagggagc ccaggggctc tgacattgct ggcaccacct ccaccctcca ggagcagatt    720
ggctggatga ccaacaaccc ccccatccct gtgggggaaa tctacaagag gtggatcatc    780
ctgggcctga acaagattgt gaggatgtac tcccccacct ccatcctgga catcaggcag   840
ggccccaagg agcccttcag ggactatgtg gacaggttct acaagaccct gagggctgag   900
caggcctccc aggaggtgaa gaactggatg acagagaccc tgctggtgca gaatgccaac    960
cctgactgca gaccatcct gaaggccctg ggccctgctg ccaccctgga ggagatgatg     1020
acagcctgcc agggggtggg gggccctggt cacaaggcca gggtgctggc tgaggccatg    1080
```

-continued

```
tcccaggtga ccaactccgc caccatcatg atgcagaggg gcaacttcag gaaccagagg    1140
aagacagtga agtgcttcaa ctgtggcaag gtgggccaca ttgccaagaa ctgtagggcc    1200
cccaggaaga agggctgctg gaagtgtggc aaggagggcc accagatgaa ggactgcaat    1260
gagaggcagg ccaacttcct gggcaaaatc tggccctccc acaagggcag gcctggcaac    1320
ttcctccagt ccaggcctga gcccacagcc cctcccgagg agtccttcag gtttggggag    1380
gagaagacca cccccagcca gaagcaggag cccattgaca aggagctgta cccctggcc    1440 tccctgaggt ccctgtttgg caacgacccc tcctcccagt aa                       1482
```